(12) United States Patent
Bouhnik

(10) Patent No.: US 12,061,297 B2
(45) Date of Patent: Aug. 13, 2024

(54) ADJUSTABLE DETECTOR ARRAY FOR A NUCLEAR MEDICINE IMAGING SYSTEM

(71) Applicant: GE Precision Healthcare LLC, Milwaukee, WI (US)

(72) Inventor: Jean-Paul Bouhnik, Zichron Yaakov (IL)

(73) Assignee: GE PRECISION HEALTHCARE LLC, Waukesha, WI (US)

(*) Notice: Subject to any disclaimer, the term of this patent is extended or adjusted under 35 U.S.C. 154(b) by 1017 days.

(21) Appl. No.: 16/747,191

(22) Filed: Jan. 20, 2020

(65) Prior Publication Data

US 2021/0219937 A1 Jul. 22, 2021

(51) Int. Cl.
*A61B 6/03* (2006.01)
*A61B 6/00* (2006.01)
(Continued)

(52) U.S. Cl.
CPC .............. *G01T 1/161* (2013.01); *A61B 6/037* (2013.01); *A61B 6/0407* (2013.01); *A61B 6/06* (2013.01);
(Continued)

(58) Field of Classification Search
CPC .. A61B 6/03; A61B 6/037; A61B 6/06; A61B 6/42; A61B 6/4208; A61B 6/4241; A61B 6/4258; A61B 6/4266; A61B 6/4275; A61B 6/54; A61B 6/542; A61B 6/544; A61B 6/545; A61B 6/547; A61B 6/08; G01T 1/16; G01T 1/1606; G01T 1/161; G01T 1/1614; G01T 1/1618; G01T 1/24; G01T 1/243; G01T 1/248; G01T 1/249; G01T 1/29; G01T 1/2907; G01T 1/2914; G01T 1/2921; G01T 1/2928;
(Continued)

(56) References Cited

U.S. PATENT DOCUMENTS

| 5,107,121 A * | 4/1992 | Lim ...................... G01T 1/1648 250/363.04 |
| 6,583,420 B1 * | 6/2003 | Nelson ................. A61B 6/4258 250/397 |

(Continued)

OTHER PUBLICATIONS

Bouhnik, J., "Adjustable Detector Array for a Nuclear Medicine Imaging System," U.S. Appl. No. 16/747,155, filed Jan. 20, 2020, 45 pages.
(Continued)

*Primary Examiner* — Allen C. Ho
(74) *Attorney, Agent, or Firm* — McCoy Russell LLP

(57) ABSTRACT

Methods and systems are provided for a medical imaging system having a detector array. In one example, the detector array may include a plurality of adjustable imaging detectors arranged in subsets thereof, each of the plurality of adjustable imaging detectors including a detector unit, each detector unit having a plurality of rows of detector modules, wherein the plurality of adjustable imaging detectors may be arranged on an annular gantry, where an inner surface of the annular gantry may circumscribe a substantially rectangular aperture therethrough, and wherein each subset of the plurality of adjustable imaging detectors may be respectively disposed on a side of the inner surface and may extend within the substantially rectangular aperture.

19 Claims, 9 Drawing Sheets

(51) Int. Cl.
   *A61B 6/04* (2006.01)
   *A61B 6/06* (2006.01)
   *A61B 6/42* (2024.01)
   *A61B 6/58* (2024.01)
   *G01T 1/161* (2006.01)
   *G01T 1/24* (2006.01)
   *G01T 1/29* (2006.01)

(52) U.S. Cl.
   CPC .......... *A61B 6/4208* (2013.01); *A61B 6/4258* (2013.01); *A61B 6/4266* (2013.01); *A61B 6/4275* (2013.01); *A61B 6/544* (2013.01); *A61B 6/588* (2013.01); *G01T 1/1614* (2013.01); *G01T 1/243* (2013.01); *G01T 1/249* (2013.01); *G01T 1/2928* (2013.01)

(58) Field of Classification Search
   CPC ... G01T 1/1611; G01T 1/1612; G01T 1/1615; G01T 1/1617
   USPC ............. 378/19, 98.8, 189, 206; 250/363.02, 250/363.03, 363.04, 363.05, 363.08, 250/363.1, 370.09
   See application file for complete search history.

(56) References Cited

U.S. PATENT DOCUMENTS

| | | | | |
|---|---|---|---|---|
| 7,147,372 B2* | 12/2006 | Nelson | A61B 6/4233 378/207 |
| 7,262,415 B2* | 8/2007 | Crosetto | A61B 6/037 250/363.04 |
| 7,864,917 B2* | 1/2011 | Ribbing | G01N 23/046 378/57 |
| 8,386,011 B2* | 2/2013 | Wieczorek | A61B 5/1127 600/407 |
| 8,552,389 B2* | 10/2013 | Jansen | A61B 6/4291 250/363.1 |
| 8,575,555 B2* | 11/2013 | Wangerin | A61B 6/037 250/363.05 |
| 8,824,635 B2* | 9/2014 | Tkaczyk | G01T 7/005 378/207 |
| 9,029,791 B1* | 5/2015 | Kovalski | G06T 11/005 250/369 |
| 9,144,411 B2* | 9/2015 | Tsukerman | A61B 6/4452 |
| 9,192,346 B2* | 11/2015 | Zingerman | A61B 6/4417 |
| 9,402,595 B2* | 8/2016 | Steinfeld | A61B 6/4266 |
| 9,442,197 B2 | 9/2016 | Shahar | |
| 9,480,441 B2* | 11/2016 | Sachs | A61B 6/037 |
| 9,554,489 B2* | 1/2017 | Hefetz | G01T 1/1648 |
| 9,579,072 B1* | 2/2017 | Grobshtein | A61B 6/0487 |
| 9,662,079 B2 | 5/2017 | Rafaeli et al. | |
| 9,693,744 B2* | 7/2017 | Rafaeli | A61B 6/4452 |
| 9,763,631 B2* | 9/2017 | Hefetz | A61B 6/0407 |
| 9,801,597 B2* | 10/2017 | Bouhnik | A61B 6/035 |
| 9,895,113 B2* | 2/2018 | Bouhnik | A61B 6/037 |
| 9,915,737 B2* | 3/2018 | Grobshtein | A61B 6/467 |
| 10,143,437 B2* | 12/2018 | Hefetz | A61B 6/52 |
| 10,145,964 B1* | 12/2018 | Shahar | H01L 31/0296 |
| 10,148,133 B2 | 12/2018 | Leabman et al. | |
| 10,188,358 B2* | 1/2019 | Levin | A61B 6/461 |
| 10,213,174 B1* | 2/2019 | Grobshtein | A61B 6/4266 |
| 10,247,834 B1* | 4/2019 | Shahar | G01T 1/241 |
| 10,278,657 B2* | 5/2019 | Peretz | A61B 6/037 |
| 10,324,200 B2* | 6/2019 | Shahar | H01L 27/14696 |
| 10,324,202 B1* | 6/2019 | Shahar | G01T 1/247 |
| 10,478,133 B2* | 11/2019 | Levy | A61B 6/585 |
| 10,478,134 B2* | 11/2019 | Carmi | G16H 30/40 |
| 10,481,285 B1* | 11/2019 | Shahar | G01T 1/24 |
| 10,492,745 B2* | 12/2019 | Bouhnik | A61B 6/544 |
| 10,575,802 B2* | 3/2020 | Bouhnik | A61B 6/4291 |
| 10,656,291 B2* | 5/2020 | Grobshtein | A61B 6/037 |
| 10,690,785 B2* | 6/2020 | Bouhnik | A61B 6/4057 |
| 10,761,223 B1* | 9/2020 | Hermony | A61B 6/037 |
| 10,761,224 B2* | 9/2020 | Bouhnik | G01T 1/247 |
| 10,932,746 B2* | 3/2021 | Bouhnik | A61B 6/545 |
| 10,987,069 B2* | 4/2021 | Roth | A61B 6/0407 |
| 11,020,074 B2* | 6/2021 | Kenig | A61B 5/0064 |
| 11,096,651 B2* | 8/2021 | Steinfeld | G01T 7/005 |
| 11,151,758 B2* | 10/2021 | Grobshtein | A61B 6/4476 |
| 11,229,414 B2* | 1/2022 | Sachs | A61B 6/0487 |
| 11,285,663 B2* | 3/2022 | Bouhnik | B29C 64/153 |
| 11,337,660 B2* | 5/2022 | Zilberstien | A61B 6/105 |
| 11,372,120 B2* | 6/2022 | Iniewski | G01T 1/249 |
| 11,406,335 B2* | 8/2022 | Bouhnik | A61B 6/037 |
| 11,426,135 B2* | 8/2022 | Vija | A61B 6/4266 |
| 11,701,074 B2* | 7/2023 | Vija | A61B 6/483 378/19 |
| 2015/0094574 A1 | 4/2015 | Bouhnik et al. | |

OTHER PUBLICATIONS

Sachs, J., "Adjustable Detector Array for a Nuclear Medicine Imaging System," U.S. Appl. No. 16/747,268, filed Jan. 20, 2020, 58 pages.

\* cited by examiner

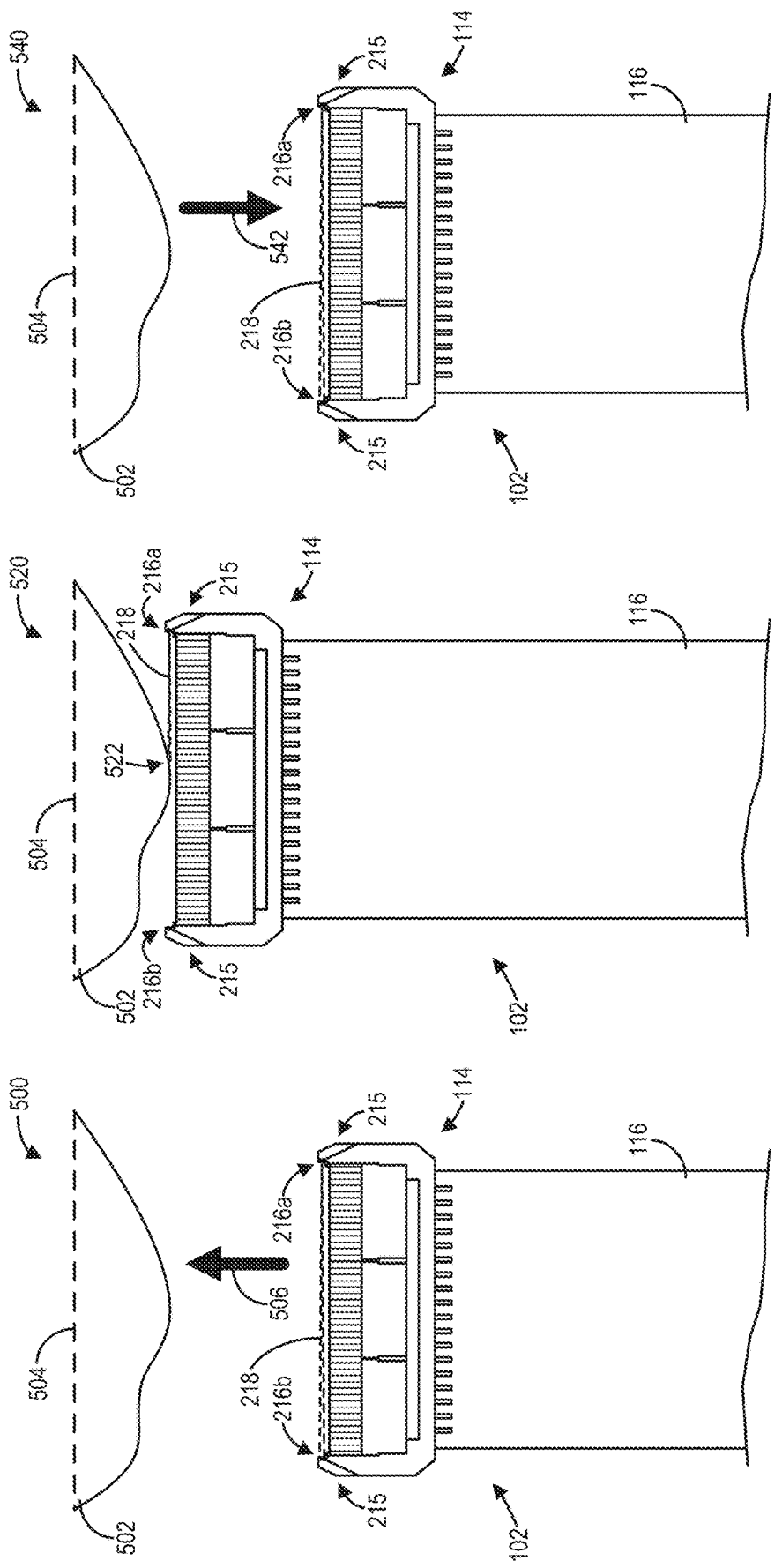

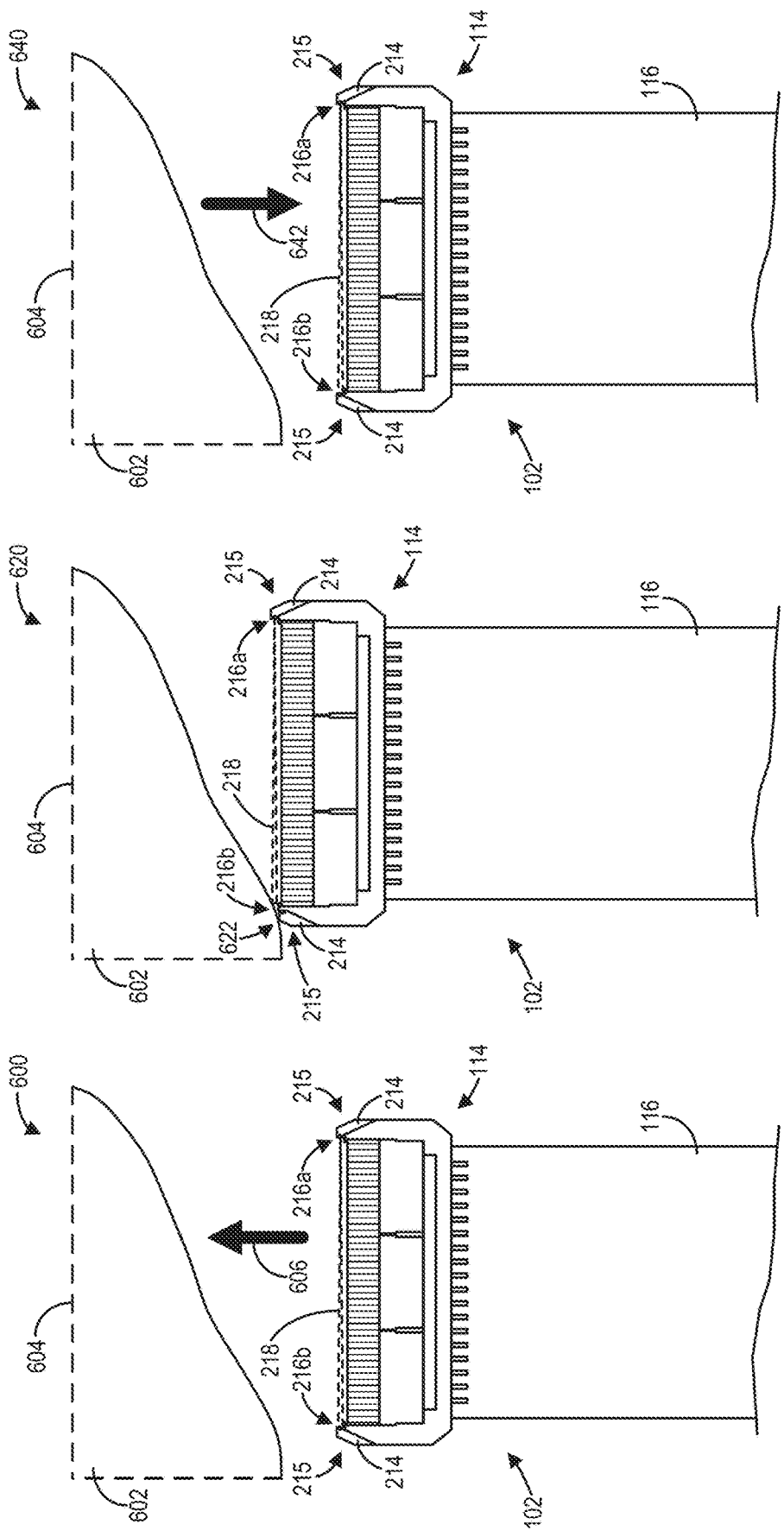

ADJUSTABLE DETECTOR ARRAY FOR A NUCLEAR MEDICINE IMAGING SYSTEM

FIELD

Embodiments of the subject matter disclosed herein relate to medical imaging systems, and more particularly to an adjustable detector array for nuclear medicine imaging systems.

BACKGROUND

Nuclear medicine (NM) imaging systems may include multiple detectors or detector heads for imaging a subject, such as a patient. For example, the detectors may be positioned adjacent to the subject on a gantry to acquire NM imaging data (e.g., radioactivity) with a wide field of view. The acquired NM imaging data may then be used to generate a three-dimensional (3D) image of the subject. Some NM imaging systems may have moving detector heads, such as gamma cameras, positioned to focus on a region of interest. One or more of the gamma cameras may be moved (for example, translated) to different positions to acquire the NM imaging data. In one example, a detector array may include a plurality of detectors dispersed around the gantry, which may each be moved (e.g., translated and/or rotated) in close proximity to the subject to increase an imaging sensitivity. However, the close proximity may present physical (e.g., pinching) or mental (e.g., claustrophobia) discomfort for the subject. Further, the imaging sensitivity may be fundamentally limited by a specific configuration of cadmium zinc telluride (CZT) modules included in each detector. For example, each detector may include a single row of CZT modules.

BRIEF DESCRIPTION

In one embodiment, a detector array may include a plurality of adjustable imaging detectors arranged in subsets thereof, each of the plurality of adjustable imaging detectors including a detector unit, each detector unit having a plurality of rows of detector modules, wherein the plurality of adjustable imaging detectors may be arranged on an annular gantry, where an inner surface of the annular gantry may circumscribe a substantially rectangular aperture therethrough, and wherein each subset of the plurality of adjustable imaging detectors may be respectively disposed on a side of the inner surface and may extend within the substantially rectangular aperture.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below:

FIGS. 5A-5C show schematic diagrams illustrating a first exemplary process for adjusting a position of the imaging detector including the detector unit, according to an embodiment;

FIGS. 6A-6C show schematic diagrams illustrating a second exemplary process for adjusting the position of the imaging detector including the detector unit, according to an embodiment;

DETAILED DESCRIPTION

Figure 1:
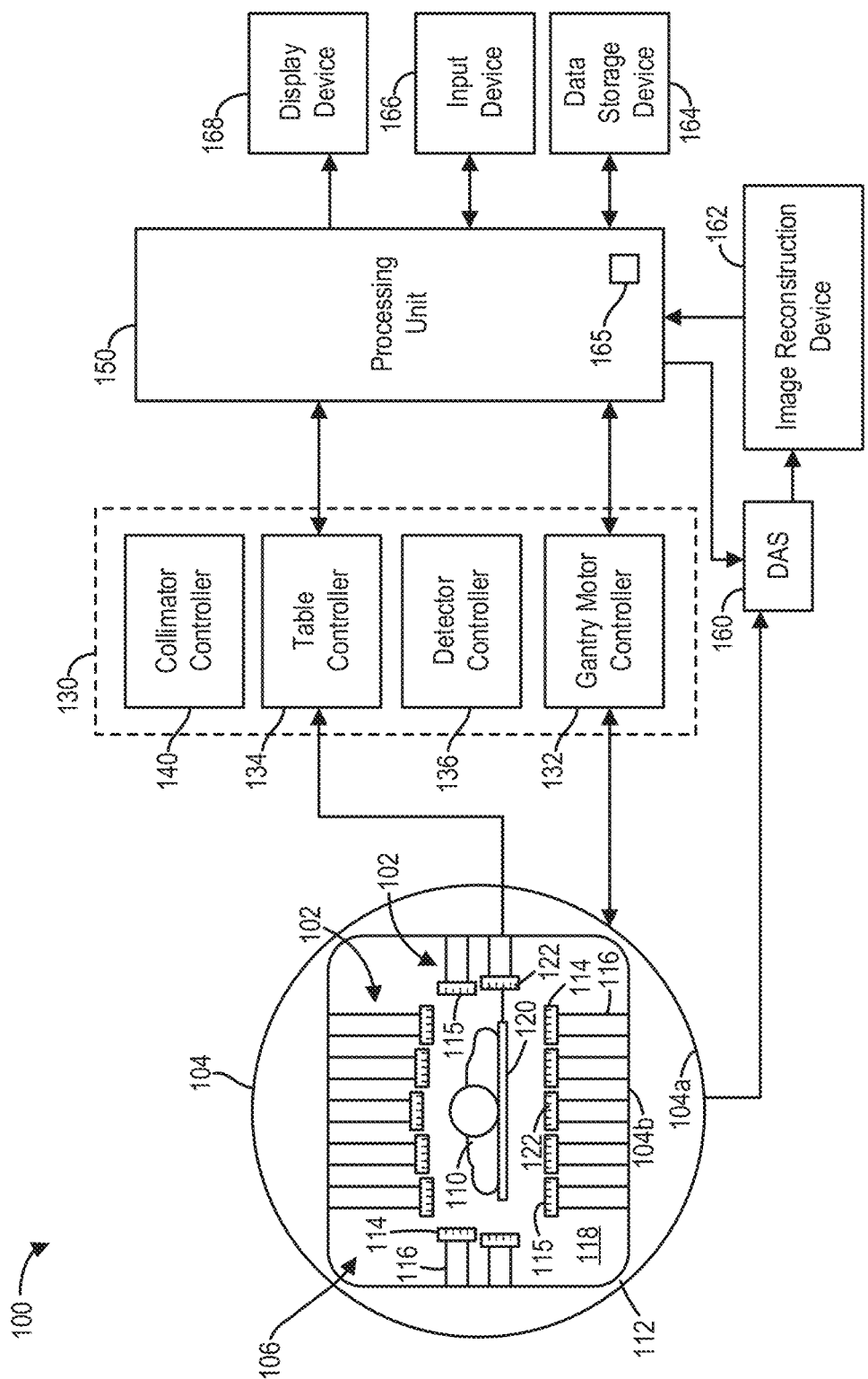
FIG. 1 shows a schematic block diagram of a nuclear medicine (NM) imaging system, according to an embodiment.

The following description relates to various embodiments of nuclear medicine (NM) imaging systems, and adjustable detector array configurations therefor. One example NM imaging system employing an exemplary detector array is depicted in FIG. 1. The detector array may include a plurality of imaging detectors, each of the plurality of imaging detectors including a respective detector unit having multiple rows of cadmium zinc telluride (CZT) modules, such as the detector unit depicted in FIG. 2. Various configurations of the detector array having subsets of varying numbers of detector units are provided in FIGS. 7A-7D.

Figure 3:
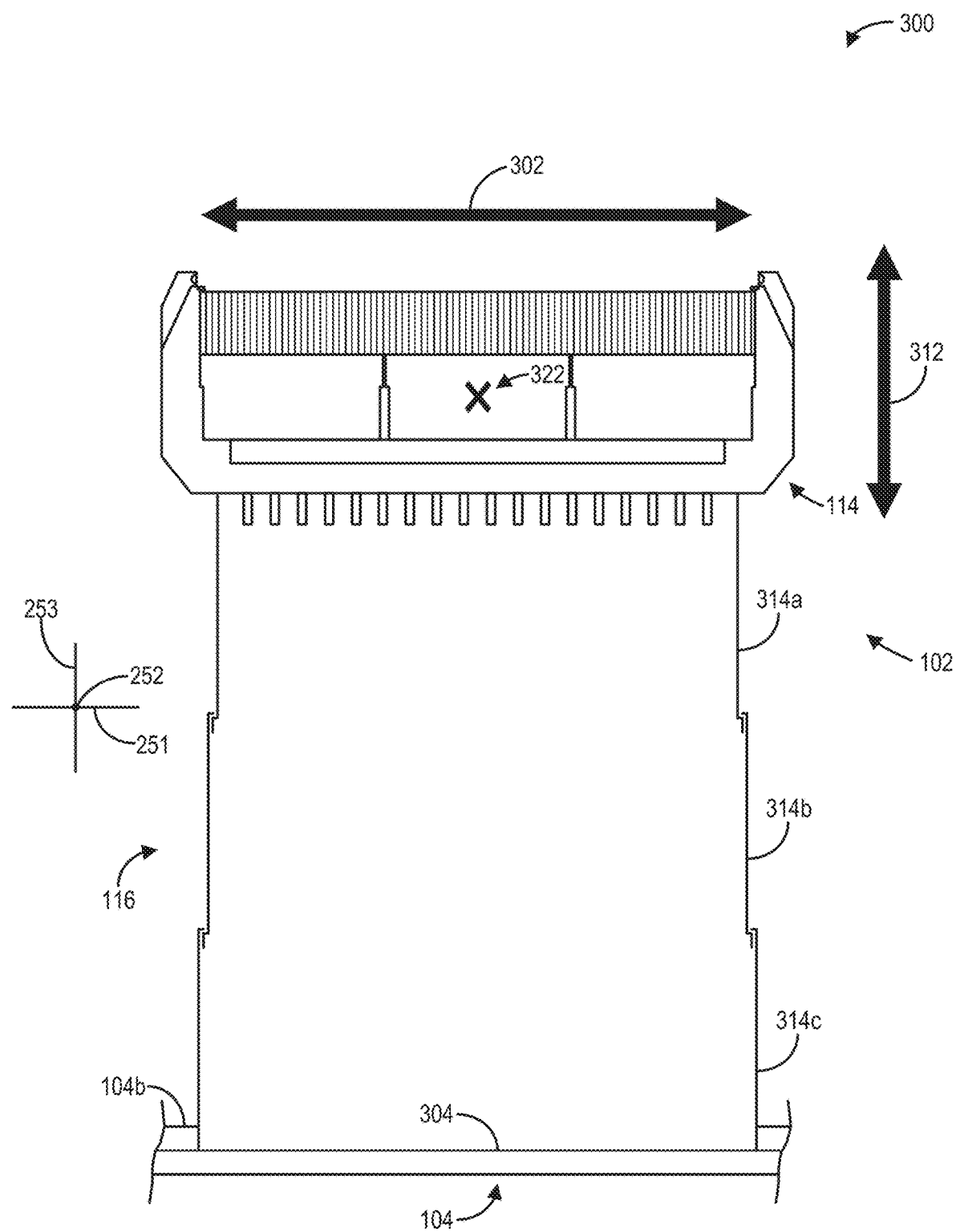
FIG. 3 shows a schematic diagram illustrating various movements of an imaging detector including the detector unit, according to an embodiment.
Figure 4B:
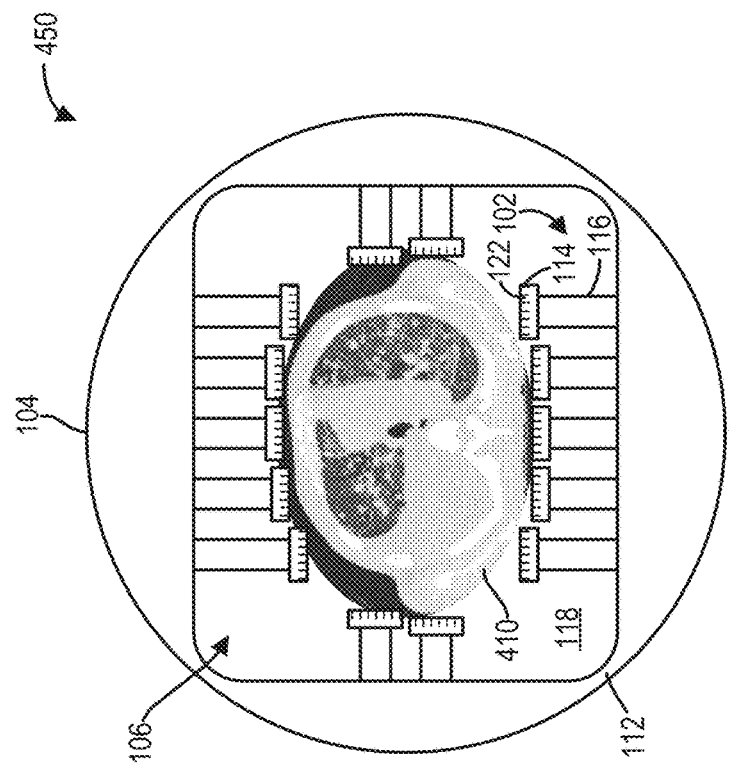
FIGS. 4A and 4B show schematic diagrams illustrating an exemplary process for conforming a detector array of the NM imaging system to a subject to be imaged, according to an embodiment.
Figure 4A:
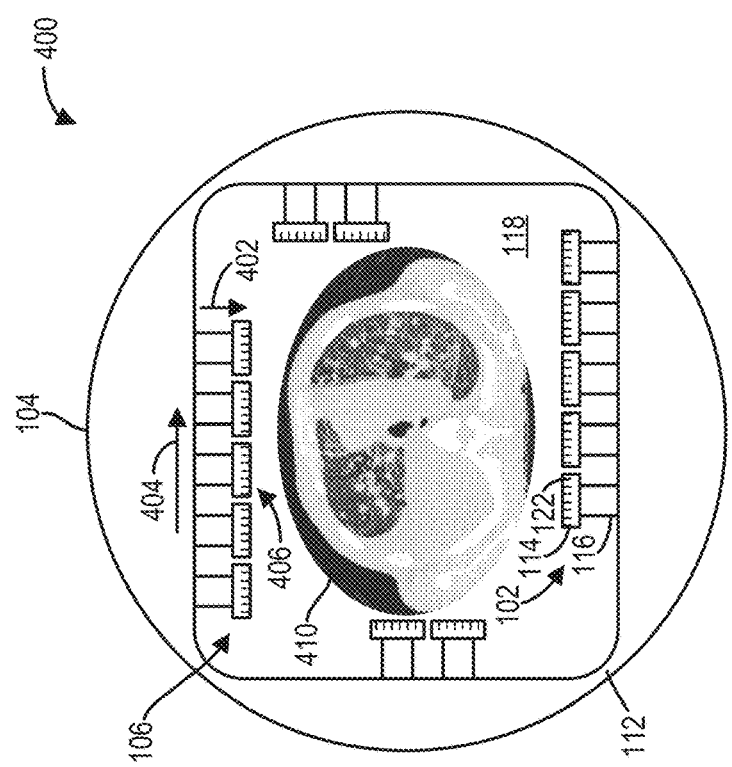
Figure 7A:
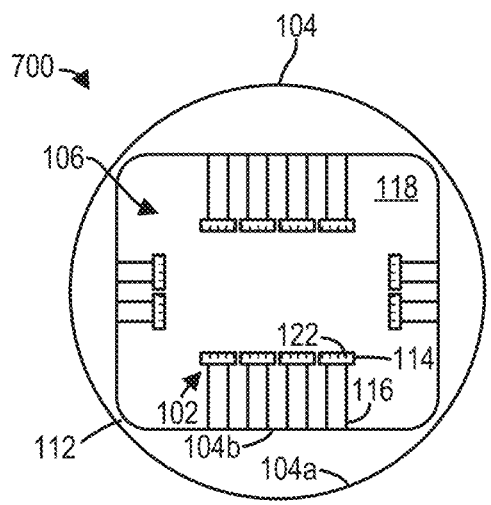
FIGS. 7A-7D show schematic diagrams illustrating exemplary configurations of the detector array, according to an embodiment.
Figure 7B:
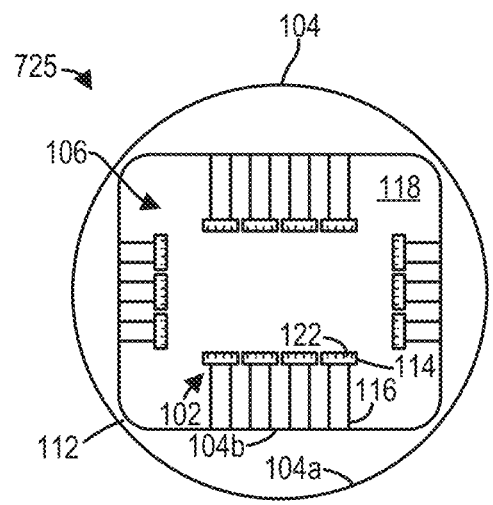
Figure 7C:
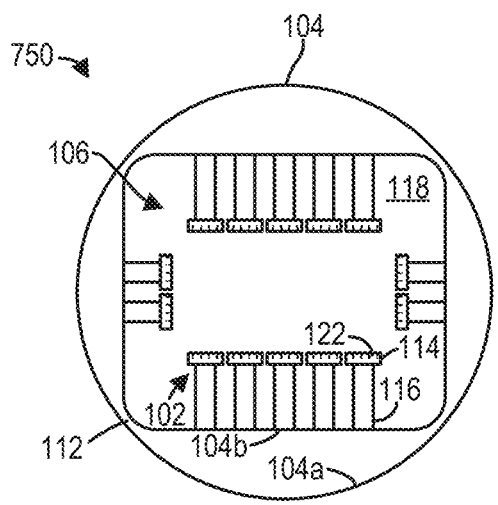
Figure 7D:
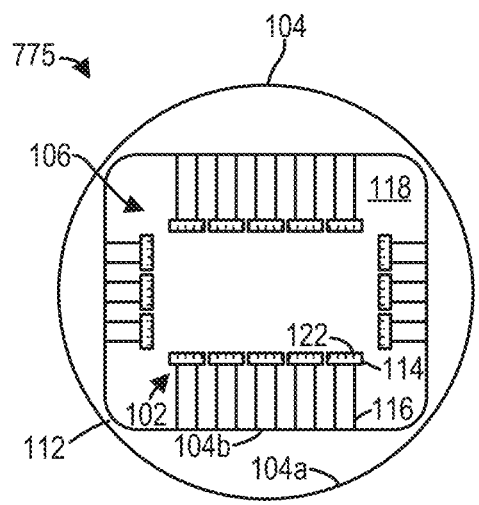

The detector unit may move along two axes of translation, as depicted in FIG. 3, so as to conform to a subject to be imaged by the NM imaging system, an exemplary process for which is depicted in FIGS. 4A and 4B. To mitigate discomfort to the subject and undue pressure to the detector unit, each detector unit may be provided with various sensors. As a first example, and as shown in FIGS. 5A-5C, a pair of optical sensors may be included in the detector unit and may project light from a light-emitting diode (LED) therebetween, such that when an object (e.g., the subject to be imaged) obscures or obstructs the LED light, the detector unit may retract. As a second example, and as shown in FIGS. 6A-6C, a pair of pressure-based sliding-end contact sensors may also be included in the detector unit and may trigger retraction of the detector unit away from an object (e.g., the subject to be imaged) when one of the sliding-end contact sensors is contacted and actuated by the object.

The detector array, and the subsets of detector units therein, may be controlled via a controller unit of the NM imaging system to conform to an outer perimeter of the subject to be imaged. Exemplary routines which may be implemented include the methods provided in FIGS. 8 and 9 for imaging the subject with sufficient angular resolution and positioning the subsets of detector units therefor.

FIG. 1 is a schematic illustration of a NM imaging system 100 having a plurality of imaging detectors mounted on a gantry. The imaging detectors may be configured to move along tracks disposed in the gantry. The movement of the imaging detectors may be controlled to reduce the likelihood of, or avoid, collision among the moving imaging detectors and/or reduce the likelihood of one imaging detector obstructing the field of view of another imaging detector. For example, the NM imaging system in some embodiments provides coordinated movement of subsets of a plurality of imaging detectors or detector heads.

In particular, a plurality of imaging detectors 102 are mounted in one or more tracks (not shown) of a gantry 104 and/or a patient support structure (not shown) (e.g., under a patient table 120), which may define a table support for the patient table 120. In the illustrated embodiment, the imaging detectors 102 are configured as a detector array 106 positioned around the subject 110 (e.g., a patient), as viewed in FIG. 1. The detector array 106 may be coupled directly to the gantry 104, or may be coupled via support members 112 thereto, to allow movement of the entire detector array 106, or subsets of the imaging detectors 102 thereof, relative to the gantry 104 (e.g., translational movement along one of the one or more tracks). As described herein, the imaging detectors 102 may be controlled to move independently of each other along the track. Additionally or alternatively, subsets of the imaging detectors 102 may be controlled to move independently of each other along the track. Further, each of the imaging detectors 102 may include a detector unit 114, each of which may be mounted to a movable detector carrier 116 (e.g., a support arm or actuator that may be driven by a motor to cause movement thereof) that extends from the gantry 104. Thus, the imaging detectors 102 may extend within an aperture 118 of the gantry 104. Specifically, the imaging detectors 102 may extend orthogonally toward a rotational axis located at a center of the gantry 104 and tracing a length of the aperture 118 thereof. In some embodiments, a detector unit 114 may be positioned outside of (e.g., at an end of) a respective movable detector carrier 116 nearest a center of the aperture 118 (e.g., the center of the gantry 104). Specifically, each of the detector unit 114 may be respectively affixed to the end of each movable detector carrier 116, such that the detector unit 114 may remain in a fixed position relative to the end of a corresponding movable detector carrier 116.

In some embodiments, the detector carriers 116 may allow movement of the detector units 114 toward and away from the subject 110, such as linearly. Thus, in the illustrated embodiment, the detector array 106 is around the subject 110 and may allow linear movement of the detector units 114, such as toward or away from the patient table 120 in one embodiment. However, other configurations and orientations are possible as described herein, as well as different types of movements (e.g., transverse or perpendicular movement relative to the patient table 120). It should be noted that the movable detector carrier 116 may be any type of support that allows movement of the detector units 114 relative to the support member 112 and/or gantry 104, which in various embodiments allows the detector units 114 to move linearly toward and away from the support member 112, such as radially inward and outwards for positioning adjacent the subject 110. For example, as described herein, the detector units 114 may be controlled to move independently of each other toward or away from the subject 110.

Each of the imaging detectors 102 in various embodiments may be smaller than a conventional whole body or general purpose imaging detector. A conventional imaging detector may be large enough to image most or all of a width of a patient's body at one time and may have a diameter of approximately 50 cm or more. In contrast, each of the imaging detectors 102 may include one or more detector units 114 coupled to respective detector carrier(s) 116 and having dimensions of 4 cm to 32 cm and may be formed of a plurality of CZT tiles or modules. As an example, each of the detector units 114 may be 16× 32 cm in size and may be composed of 21 CZT pixelated modules (not shown at FIG. 1). For example, each module may be 4×4 cm in size and have 16×16 (=256) pixels. In some embodiments, each detector unit 114 may include a plurality of modules, such as an array of 3×8 modules, 2×8 modules, 3×7 modules, or 2×7 modules, for example. However, different configurations and array sizes may be contemplated without departing from the scope of the present disclosure.

It should be understood that the imaging detectors 102 and/or detector units 114 may be different sizes and/or shapes with respect to each other, such as square, rectangular, circular, or another shape. An actual field of view (FOV) of each of the imaging detectors 102 may be directly proportional to the size and shape of the respective imaging detector 102 and detector unit 114. In some embodiments, each of the imaging detectors 102 may have a same configuration as each other imaging detector 102. Thus, in such embodiments, each of the detector units 114 respectively included in the imaging detectors 102 may have a same configuration as each other detector unit 114. In one embodiment, each of the detector units 114 may have a rectangular shape, such that each CZT module in a given row of CZT modules may be equidistant from a surface 115 of a given detector unit 114.

It will be appreciated that a number of imaging detectors 102 may vary between embodiments and is only to be limited by practical constraints and not by the exemplary embodiments discussed in the present disclosure. A lower limit of the number of imaging detectors 102 may be selected to provide a threshold amount of imaging coverage. An upper limit of the number of imaging detectors may be selected to prevent any given imaging detector 102 obscuring the FOV of another imaging detector 102. In exemplary embodiments, 10, 12, 14, 16, or 18 imaging detectors 102 may be included in the detector array 106. In additional or alternative embodiments, the number of the imaging detectors 102 included in the detector array 106 may be an even number.

The gantry 104 may be formed with the aperture 118 (e.g., opening or bore) therethrough as illustrated. The patient table 120 may be configured with a support mechanism, such as the patient support structure, to support and carry the subject 110 in one or more of a plurality of viewing positions within the aperture 118 and relative to the imaging detectors 102. Alternatively, the gantry 104 may include a plurality of gantry segments (not shown), each of which may independently move a given support member 112 or one or more of the imaging detectors 102.

The gantry 104 may also be configured in other shapes, such as a "C," "H," or "L," for example, and may be rotatable about the subject 110. For example, the gantry 104 may be formed as a closed ring or circle, or as an open arc or arch which allows the subject 110 to be easily accessed while imaging and facilitates loading and unloading of the subject 110, as well as reducing claustrophobia in some subjects 110. For example, in some embodiments the gantry 104 may be arc-shaped and the support members 112 movable along the arc to position the detector units 114 at different locations along the gantry 104. In some embodiments, the imaging detectors 102 may also be independently movable along the gantry 104. In additional or alternative embodiments, the imaging detectors 102 may also be independently movable in subsets along the gantry 104. As an example, the imaging detectors 102 may move in two subsets of five imaging detectors 102 and two subsets of two imaging detectors 102. As another example, the imaging detectors 102 may move in two subsets of five imaging detectors 102 and two subsets of three imaging detectors 102. As another example, the imaging detectors 102 may move in two subsets of four imaging detectors 102 and two subsets of two imaging detectors 102. As another example, the imaging detectors 102 may move in two subsets of four imaging detectors 102 and two subsets of three imaging detectors 102.

In the depicted embodiment, the gantry 104 is shown having a substantially circular (for example, cylindrical) outer surface 104a and a substantially rectangular (for example, rectangular prismatic) inner surface 104b. As used herein with respect to the inner surface 104b or the aperture 118, "substantially rectangular" may refer to a configuration having a cross section within 5% of a rectangular shape, wherein each angle defining the rectangular shape may be within 5% of 90° and each corner defining the rectangular shape may be a continuous edge (e.g., rounded) or two discontinuous edges (e.g., sharp). Further, the inner surface 104b may have a plurality of sides, whereby each of the plurality of sides may correspond to one of four sides of the substantially rectangular configuration. As such, each detector unit 114 may be parallel or perpendicular with each of the plurality of sides of the inner surface 104b, and thus each detector unit 114 may also be parallel or perpendicular with each other detector unit 114. Upon rotation of the gantry 104, the outer surface 104a may thus retain the cross-sectional dimensions shown at FIG. 1, while the inner surface 104b may change configurations relative to that shown at FIG. 1 (e.g., the substantially rectangular configuration may rotate from an initial configuration to a final configuration, where the final configuration may not superimpose the initial configuration). In this way, an overall angular sensitivity of the imaging detectors 102 may be enhanced via collective rotation of the imaging detectors 102 and the imaging detectors 102 may retain translational freedom of movement along the one or more tracks of the gantry 104. Further, placement of the imaging detectors 102 along sides of the rectangular inner surface 104b allows for pairs of imaging detectors 102 to be arranged closer to one another than were the pairs of imaging detectors 102 arranged radially (e.g., if the inner surface 104b was concentrically circular with the outer surface 104a). In this way, more imaging detectors 102 may be positioned per unit area of the inner surface 104b.

Additional imaging detectors (not shown) may be positioned to form rows of detector arrays or an arc or ring around the subject 110. By positioning multiple imaging detectors 102 at multiple positions with respect to the subject 110, such as along an imaging axis (e.g., head-to-toe direction of the subject 110), image data specific for a larger FOV may be acquired more quickly.

Each of the detector units 114 may include a radiation detection face, which may be directed toward the subject 110 or a region of interest within the subject 110. The radiation detection faces may each be covered by or have coupled thereto a collimator 122. The actual FOV for each of the imaging detectors 102 may be increased, decreased, or relatively unchanged by the type of collimator 122. In one embodiment, the collimator 122 is a multi-bore collimator, such as a parallel-hole collimator. However, other types of collimators, such as converging or diverging collimators may optionally or alternatively be used. Other examples for the collimator 122 include slanthole, pinhole, parallel-beam converging, diverging fan-beam, converging or diverging cone-beam, multi-bore converging, multi-bore converging fan-beam, multi-bore converging cone-beam, multi-bore diverging, or other types of collimators.

The detector units 114 may be configured such that a given collimator 122 may be exchanged for another collimator, e.g., to suit a different application. For example, a slanthole collimator may be used to direct radiation to and from an organ partially blocked from view. As another example, a pinhole collimator may be used to image a relatively small structure, such as a thyroid or a joint. In some embodiments, a given detector unit 114 may be fit with one type of collimator 122 and another detector unit 114 may be fit with another type of collimator 122. It will therefore be appreciated that many configurations of collimators 122 may be contemplated and implemented within the scope of the present disclosure. In this way, a breadth of imaging applications may be increased by varying types and configurations of collimators 122 in the detector units 114.

Optionally, multi-bore collimators may be constructed to be registered with pixels of the detector units 114, which in one embodiment are CZT detectors. However, other materials may be used. Registered collimation may improve spatial resolution by forcing photons going through one bore to be collected primarily by one pixel. Additionally, registered collimation may improve a sensitivity and energy response of pixelated detectors as detector area near the edges of a pixel or in between two adjacent pixels may have reduced sensitivity or decreased energy resolution or other performance degradation. Having collimator septa directly above the edges of pixels reduces the chance of a photon impinging at these degraded performance locations, without decreasing the overall probability of a photon passing through the collimator. Further, in some embodiments, the detector units 114 may not be fit to external covers. As such, the detector units 114 may move such that a surface thereof is as close as possible to the subject 110, thereby increasing an imaging sensitivity of the NM imaging system 100.

In some embodiments, the detector units 114 may each be provided with a plurality of proximity detectors (not shown at FIG. 1, but described in detail below with reference to FIG. 2). Each of the plurality of proximity detectors may include respective pressure sensors, optical sensors, capacitive sensors, and/or ultrasound sensors disposed at each corner of the surface 115. Feedback from a sensor included in a given detector unit 114 may indicate that the given detector unit 114 is within a threshold distance of the subject 110, the patient table 120, or another detector unit 114, and the given detector unit 114 may automatically retract or otherwise move. In additional or alternative embodiments, an LED beam may be projected between the pair of sensors. In such embodiments, if the LED beam is interrupted, the corresponding detector unit 114 may automatically retract or otherwise move (as described in detail below with reference to FIGS. 5A-6C). In additional or alternative embodiments, automatic body contouring may be implemented via optical feedback, such that an outer perimeter of the subject 110 may be approximated and the detector units 114 may automatically avoid the subject 110.

A controller unit 130 may control the movement and positioning of the patient table 120, imaging detectors 102, gantry 104, and/or the collimators 122. A range of motion before or during an acquisition, or between different image acquisitions, is set to maintain the actual FOV of each of the imaging detectors 102 directed, for example, toward or "aimed at" a particular area or region of the subject 110 or along the entire subject 110.

The controller unit 130 may have a gantry motor controller 132, table controller 134, detector controller 136, and collimator controller 140. The controllers 132, 134, 136, 140 (that is, the controller unit 130) may be automatically commanded by a processing unit 150, manually controlled by an operator, or a combination thereof. The gantry motor controller 132 may move the imaging detectors 102 with respect to the subject 110, for example, individually, in segments or subsets, or simultaneously in a fixed relationship to one another, along the one or more tracks of the gantry 104. For example, in some embodiments, the gantry motor controller 132 may cause the imaging detectors 102 and/or one or more of the support members 112 to rotate about the subject 110, which may include motion of less than or up to 180 degrees (or more).

The table controller 134 may move the patient table 120 to position the subject 110 relative to the imaging detectors 102. The patient table 120 may be moved in up-down directions, in-out directions, and right-left directions, for example. As a specific example, a large region of interest of the subject 110 (e.g., metastasis) may be imaged with relatively few imaging detectors 102 by moving the patient table 120 through an area of the gantry 104 having the imaging detectors 102 such that the same imaging detectors 102 may perform a scan of the entire region of interest. Further, an increased angular resolution of the detector array 106 may be achieved by adjusting a position of the patient table 120. Specifically, the imaging detectors 102 may be commanded by the gantry motor controller 132 and the detector controller 136 to remain in a fixed position, such that adjusting the position of the patient table 120 via the table controller 134 may corresponding adjust a relative positional relationship between the imaging detectors 102 and the patient table 120. As such, image sampling of imaging detectors 102 aligned along the gantry 104 parallel to an axis of movement of the patient table 120 may be increased, thereby increasing the angular resolution of the entire detector array 106.

The detector controller 136 may control movement of the imaging detectors 102 to move closer to and farther from a surface of the subject 110 such as by controlling translating movement of the detector carriers 116 linearly toward or away from the subject 110 (e.g., sliding or telescoping movement). Additionally or alternatively, the detector controller 136 may allow coordinated translational movement of the detector array 106, or subsets of the imaging detectors 102 thereof, in the one or more tracks of the gantry 104, and independent of movement of the gantry 104. The collimator controller 140 may adjust a position of an adjustable collimator, such as a collimator with adjustable strips (or vanes) or adjustable pinhole(s).

It should be noted that motion of one or more imaging detectors 102 may be in directions other than strictly axially or radially, and optionally, motions in several motion directions may be used. Moreover, the motions of the imaging detectors 102 are coordinated in various embodiments as described herein. Therefore, the term "motion controller" may be used to indicate a collective name for all motion controllers (e.g., controllers 132, 136). It should be noted that the various controllers may be combined, for example, the gantry motor controller 132 and detector controller 136 may be combined to provide the different movements described herein.

Prior to acquiring an image of the subject 110 or a portion of the subject 110, the imaging detectors 102, gantry 104, patient table 120, and/or collimators 122 may be adjusted as discussed in more detail herein, such as to first or initial imaging positions, as well as subsequent imaging positions. The imaging detectors 102 may each be positioned to image a portion of the subject 110. Alternatively, one or more of the imaging detectors 102 may not be used to acquire data. Positioning may be accomplished manually by the operator and/or automatically, which may include using other images acquired before the current acquisition, such as by another imaging modality such as computed tomography (CT), magnetic resonance imaging (MRI), x-ray, positron emission tomography (PET), or ultrasound. Additionally, the detector units 114 may be configured to acquire non-NM data, such as x-ray CT data.

After the imaging detectors 102, gantry 104, patient table 120, and/or collimators 122 are positioned, one or more images may be acquired by one or more of the imaging detectors 102 being used, which may include motion of the one or more of the imaging detectors 102 along the one or more tracks of the gantry 104. The image data acquired by each imaging detector 102 may be combined and reconstructed into a composite image, which may include two-dimensional (2D) images, a three-dimensional (3D) volume, or a 3D volume over time, e.g., four dimensions (4D).

In one embodiment, the imaging detectors 102, gantry 104, patient table 120, and/or collimators 122 may remain stationary after being initially positioned. In another embodiment, an effective FOV for one or more of the imaging detectors 102 may be increased by movement such as moving one or more of the imaging detectors 102 along the one or more tracks of the gantry 104, rotating the detector array 106 with the gantry 104, adjusting one or more of the collimators 122, or moving the patient table 120.

In various embodiments, a data acquisition system (DAS) 160 may receive electrical signal data produced by the imaging detectors 102 and converts the electrical signal data into digital signals for subsequent processing. An image reconstruction device 162 and a data storage device 164 may be provided in addition to the processing unit 150. It should be noted that one or more functions related to one or more of data acquisition, motion control, data processing, and image reconstruction may be accomplished through hardware, software, and/or by shared processing resources, which may be located within or near the NM imaging system 100, or may be located remotely. Additionally, a user input device 166 may be provided to receive user inputs (e.g., control commands), as well as a display 168 for displaying images.

Additionally, a detector position controller 165 may also be provided, which may be implemented in hardware, software, or a combination thereof. For example, as shown in FIG. 1, the detector position controller 165 may form part of, or operate in connection with, the processing unit 150. In some embodiments, the detector position controller 165 may be a module that operates to control the movement of the imaging detectors 102 such that coordinated or synchronized movement is provided as described herein. It should be noted that movement of a plurality of the imaging detectors 102 may be performed at the same time (e.g., simultaneously or concurrently) or at different times (e.g., sequentially or step-wise, such as back and forth between two imaging detectors 102). It also should be understood that when referring to a detector head, such a detector head may include one or multiple detector modules (e.g., CZT modules).

Figure 2:
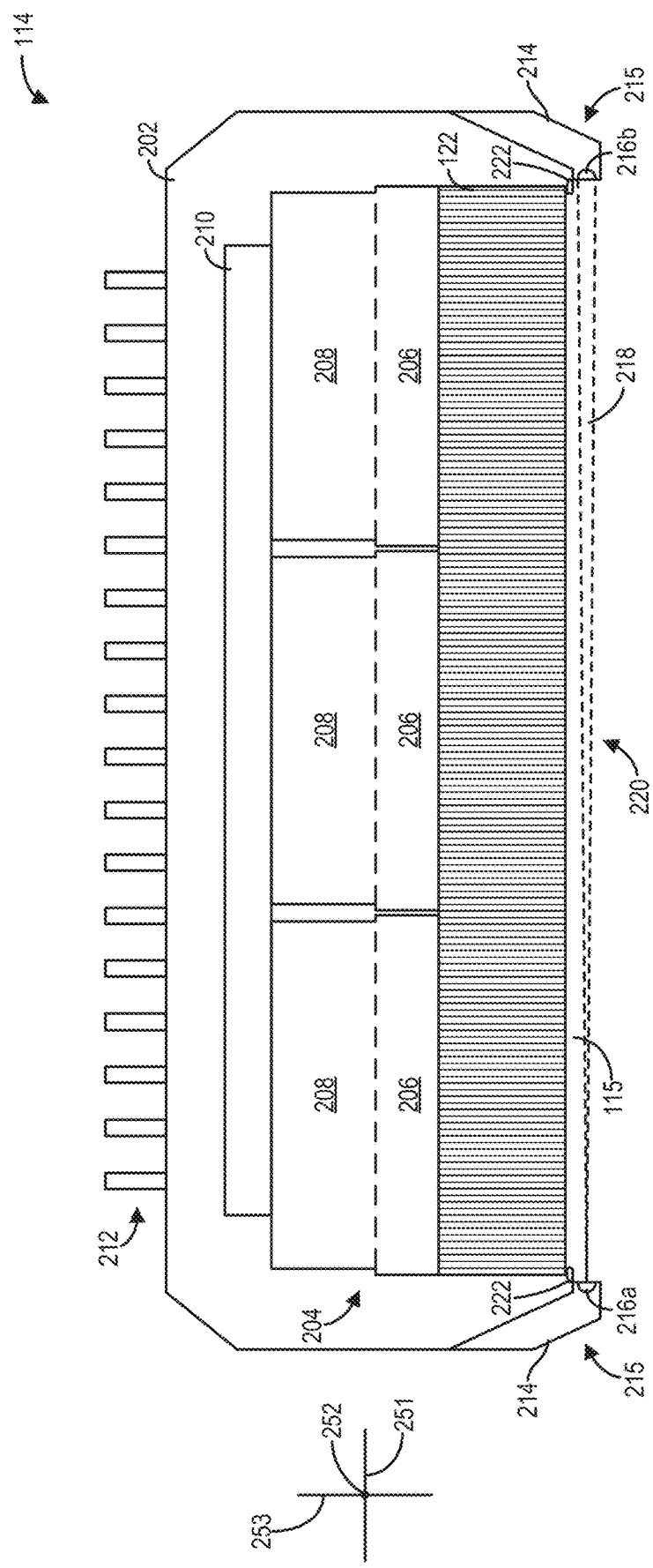
FIG. 2 shows a schematic diagram of a detector unit for use in the NM imaging system, according to an embodiment.

Referring now to FIG. 2, a cross-sectional view of the detector unit 114 is depicted, showing three CZT modules 204, each indicative of a row of multiple CZT modules 204. It will be appreciated that in FIG. 2, and in FIG. 3 (described in more detail below), mutually perpendicular axes 251, 252, and 253 define a three-dimensional space relative to the cross-sectional view, where the axis 251 and the axis 253 define a plane of the cross-sectional view and the axis 252 is normal to the plane of the cross-sectional view. Herein, the mutually perpendicular axes 251, 252, and 253 may be employed to describe an overall movement of the detector unit 114, as well as relative positioning of components of the detector unit 114 with respect to one another. For example, each of the three rows of CZT modules 204 may be respectively aligned with the depicted CZT modules 204 and may extend along the axis 252, such that one or more CZT modules 204 may be in front of the plane of the cross-sectional view and one and/or one or more CZT modules 204 may be behind the plane of the cross-sectional view.

The detector unit 114 may include a casing 202 which may house one or more of the various components of the detector unit 114, where the casing 202 may be a frame or other support structure. The casing 202 may be made of a high-density material, such as lead or tungsten, for example. The collimator 122 may be disposed within the casing 202. In specific embodiments wherein the collimator 122 is exchangeable, the collimator 122 may be removably fixed in place by a pair of adjustable locking mechanisms 222 such that the collimator 122 may be attached and detached upon application of pressure to each of the pair of adjustable locking mechanisms 222. The collimator 122 may include a plurality of septa, which may be configured to receive and narrow incoming radiation (e.g., gamma rays) for the CZT modules 204. The incoming radiation may be passed to CZT detector plates 206 respectively situated in the CZT modules 204. Each of the CZT modules 204 may further include electronics 208 (e.g., output electronics to output detected events) conductively coupling the CZT detector plate 206 to a printed circuit board (PCB) 210, such that NM imaging data may be acquired based on the incoming radiation. The NM imaging data may then be passed to the controller unit (e.g., 130) and the processing unit (e.g., 150) of the NM imaging system (e.g., 100), as described above with reference to FIG. 1. A heat sink (e.g., air or water cooling) 212 with a fan (not shown) may be disposed on, or positioned within, the casing 202, so as to prevent overheating of the various components therein during operation of the detector unit 114.

The detector unit 114 may include a pair of proximity detectors 215 such that contact with the subject (e.g., 110) by the detector unit 114 may be mitigated or avoided. As shown, the pair of proximity detectors 215 may be disposed opposite to one another, such that each of the pair of proximity detectors 215 reflects an opposite proximity detector 215 across a plane parallel to a plane including the axes 252 and 253. It will be appreciated that the pair of proximity detectors 215 may include any type of proximity sensor known in the art, such as further pressure sensors, optical sensors, capacitive sensors, and/or ultrasound sensors, within the scope of the present disclosure. For example, and as depicted at FIG. 2, the pair of proximity detectors 215 may respectively include a pair of optical sensors 216a, 216b. The optical sensor 216a may be operable to project an LED beam 218 along the axis 251 and across a cavity 220 formed by the proximity detectors 215 extending from the surface 115 along the axis 253. Assuming no obstructing or obscuring object enters the cavity 220, the LED beam 218 may correspondingly be received by the optical sensor 216b. However, in some examples, an object (e.g., a portion of the subject) may indeed enter the cavity 220. In such examples, the LED beam 218 may be prevented from reaching the optical sensor 216b. As such, appropriate movement of the detector unit 114 may be automatically actuated so that the object and/or the detector unit 114 is not subjected to undue pressure (e.g., the detector unit 114 may translate along the axis 253 away from the object, as described in detail with reference to FIGS. 5A-5C below).

Each of the pair of proximity detectors 215 may additionally or alternatively include a sliding-end contact sensor 214. The sliding-end contact sensors 214 may be actuated (e.g., depressed along the axis 253) by pressure applied thereto by an object (e.g., a portion of the subject, e.g., 110, or another detector unit 114). Thus, and as described in detail below with reference to FIGS. 6A-6C, when the object actuates at least one of the sliding-end contact sensors 214, the LED beam 218 may not reach the optical sensor 216b and appropriate movement of the detector unit 114 may be automatically actuated so that the object and/or the detector unit 114 is not subjected to undue pressure (e.g., the detector unit 114 may translate along the axis 253 away from the object).

The detector unit 114 provided by an embodiment of the present disclosure may be optimized for flexible, high-resolution NM imaging. As a first example, no obstructing external housing may be disposed around the detector unit 114, permitting the detector unit 114 to be moved as close as possible to the subject (e.g., 110) to be imaged. Indeed, the proximity detectors 215 may preclude use of such external housings, as the proximity detectors 215 may mitigate discomfort to the subject by automatically adjusting the detector unit 114 near to, but not in contact with, the subject upon actuation of at least one of the proximity detectors 215. As a second example, the multiple rows of CZT modules 204 may provide proportionally greater imaging resolution to the detector unit 114 as compared to a detector unit having a single row of CZT modules. Thus, in the depicted example, the detector unit 114, having three rows of CZT modules 204, may correspondingly have three times the imaging resolution of a detector unit having a single row of CZT modules, as the multiple rows of CZT modules 204 may provide increased image sampling. As a third example, and as described in detail below with reference to FIG. 3, the detector unit 114, and subsets of multiple detector units 114, may be configured to move along multiple degrees of freedom, facilitating conformation of the detector unit 114, and thus the entire detector array (e.g., 106), to the subject. In this way, an amount of "dead shielding" space (e.g., imaged space not corresponding to the subject) may be reduced.

Referring now to FIG. 3, a schematic diagram 300 of the imaging detector 102 including the detector unit 114 and the detector carrier 116 is depicted. Further shown are a number of degrees of freedom of the detector unit 114 which may be actuated by various mechanical components of the NM imaging system (e.g., 100) and controlled by the controller unit (e.g., 130) thereof. For example, the imaging detector 102 may be affixed to the gantry 104, or support members thereof (e.g., 112), such as a track 304. In some embodiments, the track 304 may circumscribe an inner surface 105 of the gantry 104, where the imaging detector 102 may be positioned partially within the track 304. Specifically, in some examples, the track 304 may be an open space through which the detector carrier 116 may extend from an internal rotational mechanism. In other examples, a support mechanism to facilitate movement, such as wheels, may be placed within the track and coupled to the detector carrier 116. As such, the imaging detector 102 may move with the gantry 104 or may move independently from the gantry 104 along the track 304. Further, the imaging detector 102 may extend within the aperture (e.g., 118; not shown at FIG. 3) of the gantry 104. Carried by the detector carrier 116, the detector unit 114 may therefore translate 302 along the axis 251. It will be appreciated that, in embodiments wherein the inner surface 104b of the gantry 104 is configured in a rectangular annular shape (as depicted in FIG. 1), at least some other detector units 114 may instead translate 302 along an axis normal to the axis 251 (e.g., the axis 253).

As another example, the detector carrier 116 may include a plurality of telescoping segments (e.g., 314a, 314b, 314c). The plurality of telescoping segments may collapse into one another toward the gantry 104 along the axis 253. For example, the telescoping segment 314a may collapse into the telescoping segment 314b and the telescoping segment 314b may collapse into the telescoping segment 314c, such that the plurality of telescoping segments may be in a fully collapsed, or retracted, position. The schematic diagram 300, however, depicts the plurality of telescoping segments in a fully extended position. In this way, the detector unit 114 may translate 312 along the axis 253 within physical limitations of the detector carrier 116 (e.g., the detector carrier 116 may be in any position between the fully collapsed position and the fully extended position).

In the embodiments described herein, the detector unit 114 may be one of a subset of detector units 114. Further, since the inner surface 104b of the gantry 104 may be configured as a rectangular annular shape (as described in FIG. 1) instead of a circular annular shape, the detector units 114 may be aligned closely, as translation 302 will not result in interference with, or obstruction by, adjacent detector units 114. As a result, however, the detector unit 114 may not independently pivot 322 around an axis located at a center thereof, as such close alignment of the subset including the detector unit 114 may preclude such independent pivoting motions.

In this way, the detector unit 114 may at least move about two translational axes, such that the detector array (e.g., 106) including a plurality of detector units 114 may be operable to conform to a subject to be imaged. It will be appreciated that other movements of the detector unit 114 may be contemplated and implemented by one of ordinary skill in the art, and that the present disclosure is not to be interpreted as limited to the degrees of freedom described with reference to FIG. 3.

Referring now to FIGS. 4A and 4B, schematic diagrams 400 and 450 are depicted, illustrating an exemplary process for conforming the detector array 106 to a subject 410 (represented in FIGS. 4A and 4B as a cross-sectional slice thereof). As described above with reference to FIG. 1, the detector array 106 may include a plurality of imaging detectors 102, each imaging detector 102 including the detector unit 114 and the detector carrier 116. Further, the detector array 106 may be formed within the aperture 118 of the gantry 104, whereby the detector array 106 may be directly coupled to the gantry 104 or to the support members 112 thereof.

As shown in the schematic diagram 400, the plurality of detector units 114 may be aligned in subsets thereof (e.g., of two or five), which may not be optimal for imaging of the subject 410 (as an outer perimeter of the subject 410 may not include flat, uniform sides). Further, the plurality of detector units 114 may be retracted away from the subject 410 to allow the subject 410 to freely enter the aperture 118, which may further preclude optimal imaging resolution.

Each of the plurality of detector units 114 may independently translate toward the subject 410. Further, the plurality of detector units 114 may translate in subsets along a track of the gantry 104 (such as the track 304, as described above with reference to FIG. 3). As such, the plurality of detector units 114 may move to conform to the subject 410. For example, automatic body contouring may be implemented by the NM imaging system (e.g., 100), which may estimate the outer perimeter of the subject 410. Based on respective positions thereof, each of the plurality of detector units 114 may therefore move to align toward the estimated outer perimeter. In the schematic diagram 400, for example, one of the plurality of detector units 114 is shown as translating 402 toward the subject 410. Further, the one of the plurality of detector units 114 is further shown as translating 404 simultaneously with four other detector units 114 in a subset 406 to align with the subject 410. Each remaining detector unit 114 may similarly adjust a position thereof to acquire NM imaging data of an increased imaging resolution.

As such, the plurality of detector units 114 may move to a final position, as depicted in the schematic diagram 450. In this way, the detector array 106 may be optimized for subjects of varying sizes and shapes, providing an NM imaging system with high imaging flexibility. As shown, the final position of the plurality of detector units 114 may be adjacent to, but not in contact with, the subject 410.

In some embodiments, automatic body contouring alone may not be sufficient to prevent the plurality of detector units 114 from contacting the subject 410. For example, automatic body contouring may estimate an outer perimeter of the subject 410 which, at least in part, may lie within an actual perimeter of the subject 410. Thus, when a given detector unit 114 attempts to conform to the outer perimeter estimated by the automatic body contouring, the given detector unit 114 may contact the subject 410. Such contact may be mitigated via proximity detectors (e.g., 215) included in each detector unit 114, where the proximity detectors may include optical sensors (e.g., 216a, 216b) and sliding-end contact sensors (e.g., 214) for providing feedback regarding positioning of the plurality of detector units 114 relative to an actual location of the subject 410 (that is, not based on the estimated outer perimeter alone).

Referring now to FIGS. 5A-5C, schematic diagrams 500, 520, 540 are depicted, illustrating an exemplary process for adjusting a position of the imaging detector 102 when the detector unit 114 thereof moves near a subject 502 via extension of the detector carrier 116. The detector unit 114 may include the pair of proximity detectors 215, where the pair of proximity detectors 215 may respectively include one of the optical sensors 216a, 216b. As such, feedback from the proximity detectors 215 may be utilized by the controller unit (e.g., 130) described above with reference to FIG. 1 to determine a proximity of the detector unit 114 to the subject 502. It will be appreciated that the subject 502 is depicted in the schematic diagrams 500, 520, 540 as a portion thereof, and that the subject 502 may extend beyond the dashed line 504.

As shown in the schematic diagram 500, the detector carrier 116 may extend in a direction 506, translating the detector unit 114 toward the subject 502. As described in detail above with reference to FIG. 3, the detector carrier 116 may include the plurality of telescoping segments (not shown at FIGS. 5A-5C), enabling such extension of the detector carrier 116. As further shown, the optical sensor 216a may project the LED beam 218, which may be correspondingly received by the optical sensor 216b.

After extension of the detector carrier 116, the detector unit 114 may be positioned as shown in the schematic diagram 520. As shown, a portion of the subject 502 may obstruct 522 the LED beam 218 from reaching the optical sensor 216b. As such, feedback from the optical sensor 216b, or lack thereof, may indicate that the detector unit 114 has been positioned too close to, but may not be contacting, the subject 502.

As such, and as shown in the schematic diagram 540, the detector carrier 116 may retract in the direction 542, translating the detector unit 114 away from the subject 502. The detector carrier 116 may be configured to retract to just beyond a predetermined distance from where the obstruction 522 occurred. In other examples, the detector carrier 116 may be configured to retract until the LED beam 218 is again received by the optical sensor 216b. As such, a high imaging resolution may be retained by maintaining the proximity of the detector unit 114 to the subject 502. In this way, in some examples, the detector unit 114 may automatically avoid contacting the subject 502, thereby mitigating excess pressure on the various components of the detector unit 114 and discomfort to the subject 502.

Referring now to FIGS. 6A-6C, schematic diagrams 600, 620, 640 are depicted, illustrating an exemplary process for adjusting a position of the imaging detector 102 when the detector unit 114 thereof moves near a subject 602 via extension of the detector carrier 116. The detector unit 114 may include the pair of proximity detectors 215, where the pair of proximity detectors 215 may respectively include one sliding-end contact sensor 214 and one of the optical sensors 216a, 216b. As such, feedback from the proximity detectors 215 may be utilized by the controller unit (e.g., 130) described above with reference to FIG. 1 to determine a proximity of the detector unit 114 to the subject 602. It will be appreciated that the subject 602 is depicted in the schematic diagrams 600, 620, 640 as a portion thereof, and that the subject 602 may extend beyond the dashed line 604.

As shown in the schematic diagram 600, the detector carrier 116 may extend in a direction 606, translating the detector unit 114 toward the subject 602. As described in detail above with reference to FIG. 3, the detector carrier 116 may include the plurality of telescoping segments (not shown at FIGS. 6A-6C), enabling such extension of the detector carrier 116. As further shown, the optical sensor 216a may projected the LED beam 218, which may be correspondingly received by the optical sensor 216b.

After extension of the detector carrier 116, the detector unit 114 may be positioned as shown in the schematic diagram 620. As shown, the detector unit 114 may contact 622 the subject 602, thereby actuating (e.g., depressing) one of the sliding-end contact sensors 214. Once actuated, the sliding-end contact sensor 214, being mechanically coupled to the optical sensor 216b, may move the optical sensor 216b out of a path of the LED beam 218. As such, feedback from the optical sensor 216b, or lack thereof, may indicate that the detector unit 114 has moved such that a corner thereof including one of the pair of proximity detectors 215 has contacted the subject 602.

As such, and as shown in the schematic diagram 640, the detector unit 114 may retract in the direction 642, moving the detector unit 114 away from the subject 602. The detector unit 114 may be configured to retract until the actuated sliding-end contact sensor 214 returns to a default position (e.g., the position depicted by the schematic diagrams 600, 640), such that a high imaging resolution may be retained by maintaining the proximity of the detector unit 114 to the subject 602. In this way, in some examples, the detector unit 114 may automatically retract from the subject 602 upon actuation of the sliding-end contact sensor 214 under light pressure, thereby mitigating excess pressure on the various components of the detector unit 114 and discomfort to the subject 602. It will further be appreciated that, though the pair of sliding-end contact sensors 214 are coupled with the pair of optical sensors 216a, 216b in the exemplary process depicted by FIGS. 6A-6C, that the exemplary process may be executed based on the pressure feedback received by at least one of the pair of sliding-end contact sensors 214 absent the pair of optical sensors 216a, 216b.

Referring now to FIGS. 7A-7D, schematic diagrams 700, 725, 750, 775 are depicted, showing various exemplary configurations of the gantry 104 and the detector array 106. The detector array 106 may either be affixed to the gantry 104 or to the support members 112 thereof. As shown, the detector array 106 may include the plurality of imaging detectors 102, each of the plurality of imaging detectors 102 respectively including the detector unit 114 positioned on the detector carrier 116. Each of the detector units 114 may respectively include the collimator 122 for receiving and focusing incoming radiation from a subject (not shown at FIGS. 7A-7D). In the exemplary configurations of FIGS. 7A-7D, the outer surface 104a of the gantry 104 is configured as a substantially circular ring having the rectangular aperture 118 therethrough, where the aperture 118 is circumscribed and defined by the inner surface 104b. It will be appreciated, however, that the exemplary configurations of FIGS. 7A-7D are not to be interpreted as limiting the present disclosure, and that any configuration of the detector array 106 and the gantry 104 may be contemplated and implemented by one of ordinary skill in the art.

As a first example, and as shown in the schematic diagram 700, the detector array 106 may include twelve imaging detectors 102 positioned in a default configuration (e.g., prior to movements of individual imaging detectors 102) on the gantry 104, wherein the twelve imaging detectors 102 are grouped in two subsets of four imaging detectors 102 and two subsets of two imaging detectors 102, and are spaced substantially equivalently from one another within a given subset. As a second example, and as shown in the schematic diagram 725, the detector array 106 may include fourteen imaging detectors 102 positioned in a default configuration (e.g., prior to movements of individual imaging detectors 102) on the gantry 104, wherein the fourteen imaging detectors 102 are grouped in two subsets of four imaging detectors 102 and two subsets of three imaging detectors 102, and are spaced substantially equivalently from one another within a given subset. As a third example, and as shown in the schematic diagram 750, the detector array 106 may include fourteen imaging detectors 102 positioned in a default configuration (e.g., prior to movements of individual imaging detectors 102) on the gantry 104, wherein the fourteen imaging detectors 102 are grouped in two subsets of five imaging detectors 102 and two subsets of two imaging detectors 102, and are spaced substantially equivalently from one another within a given subset. As a fourth example, and as shown in the schematic diagram 775, the detector array 106 may include sixteen imaging detectors 102 positioned in a default configuration (e.g., prior to movements of individual imaging detectors 102) on the gantry 104, wherein the sixteen imaging detectors 102 are grouped in two subsets of five imaging detectors 102 and two subsets of three imaging detectors 102, and are spaced substantially equivalently from one another within a given subset.

Figure 8:
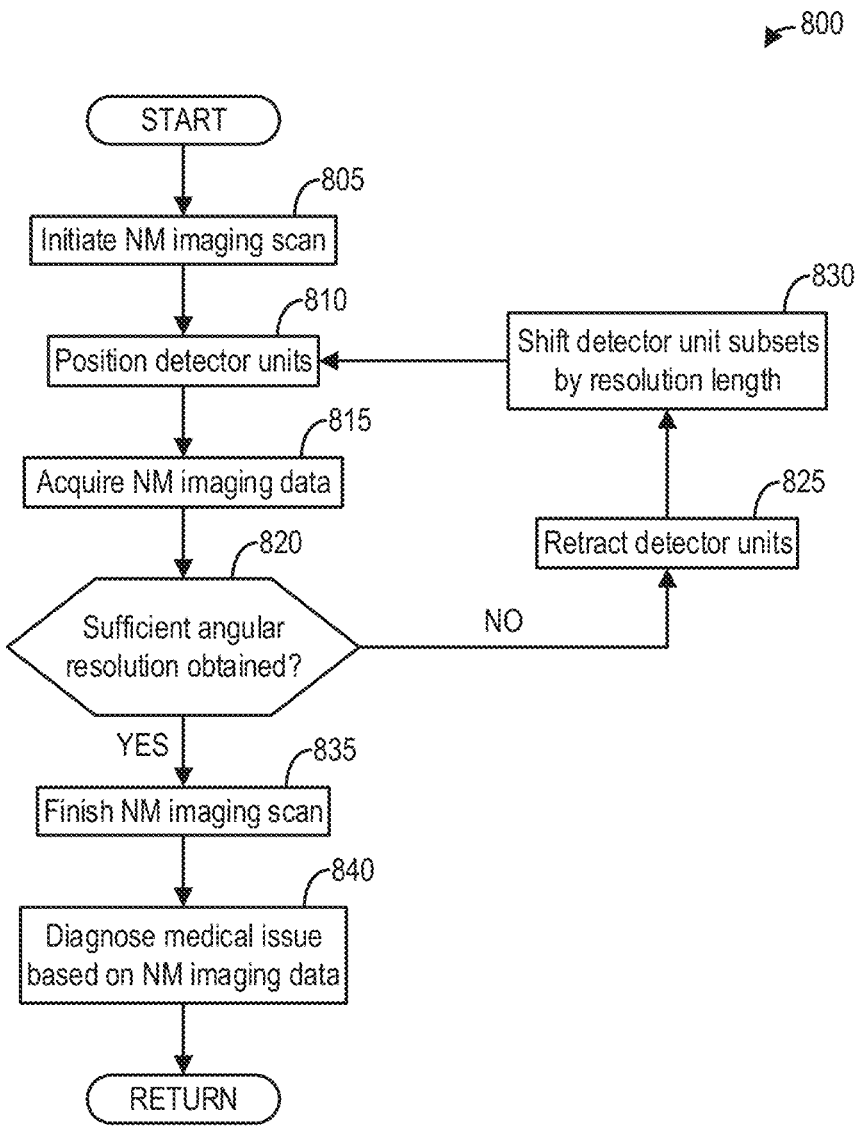
FIG. 8 shows a flow chart of a method for imaging a subject via the NM imaging system, according to an embodiment.

Referring now to FIG. 8, a flow chart is depicted, showing a method 800 for imaging a subject via an NM imaging system. Execution of the method 800 may depend upon various degrees of freedom via which detector units of the NM imaging system may move, such that the detector units are positioned to optimally image a subject.

Method 800 is described below with regard to the systems and components depicted in FIGS. 1 and 2, though it should be appreciated that method 800 may be implemented with other systems and components without departing from the scope of the present disclosure. In some embodiments, method 800 may be implemented as executable instructions in any appropriate combination of the NM imaging system 100, an edge device (e.g., an external computing device) connected to the NM imaging system 100, a cloud in communication with the NM imaging system 100, and so on. As one example, method 800 may be implemented in non-transitory memory of a computing device, such as the processing unit 150 of the NM imaging system 100 in FIG. 1 (e.g., in communication with the controller unit 130 of the NM imaging system 100).

Method 800 may begin at 805, where an NM imaging scan may be initiated. The NM imaging scan may include receiving incoming radiation from the subject (e.g., 110) at the detector units (e.g., 114). However, each of the detector units may not yet be positioned for optimal imaging by the NM imaging system (e.g., 100), and therefore, at 810, method 800 may include positioning the detector units prior to actively acquiring NM imaging data at 815. Positioning the detector units may include translating the detector units, and subsets thereof, via various degrees of freedom such that the detector units may be positioned adjacent to, but not in contact with, the subject. In this way, the detector units may be coordinated to move to a first position to receive the incoming radiation from the subject.

Once the detector units (e.g., 114) are positioned, the incoming radiation may pass through, and be narrowed by, the collimators (e.g., 122) associated with the various detector units. The incoming radiation may be passed to respective CZT modules (e.g., 204), such that, at 815, the NM imaging data may be acquired.

At 820, method 800 may include determining whether sufficient angular resolution of the NM imaging data has been obtained by the detector array (e.g., 106). In some embodiments, each of the subsets of detector units (e.g., 114) may be shifted by respective detector carriers (e.g., 116) moving along a track (such as the track 304 as described above with reference to FIG. 3) of the gantry (e.g., 104) such that individual detector units do not superimpose a prior position of any other detector unit. For example, if the detector units are disposed on the gantry with a pitch of six inches, then the subsets of detector units may translate orthogonal to the subject by less than six inches (referred to herein as a resolution length) and the subject (e.g., 110) may be reimaged to obtain further angular resolution.

Specifically, if sufficient angular resolution has not been obtained by the detector array (e.g., 106), method 800 may proceed to 825 to retract the detector units (e.g., 114) via the detector carriers (e.g., 116). In some embodiments, retracting the detector units via the detector carriers may include collapsing a plurality of telescoping segments of the detector carriers to a fully collapsed position. Once the detector units are retracted, method 800 may include, at 830, shifting each of the subsets of detector units by the resolution length. Method 800 may then return to 810 to again position the detector units for imaging. In this way, the detector units may be coordinated to move to a second position to receive further incoming radiation from the subject.

If sufficient angular resolution has been obtained by the detector array (e.g., 106), method 800 may proceed to 835 to finish the NM imaging scan (e.g., no further NM imaging data may be acquired until another NM imaging scan is initiated). Then, at 840, method 800 may include diagnosing a medical issue based on the NM imaging data. Diagnosing the medical issue may be performed by a medical professional upon analysis of the NM imaging data acquired during the NM imaging scan. For example, an area within the subject (e.g., 110) may be afflicted by a medical issue. The area within the subject may be imaged during the NM imaging scan, and the NM imaging system (e.g., 100) provided by an embodiment of the present disclosure may generate more precise and consistent NM imaging data as compared to conventional NM imaging systems. In this way, an accuracy of the diagnosis of the medical issue may be improved and may be made more consistent between medical professionals. Method 800 may then end.

Figure 9:
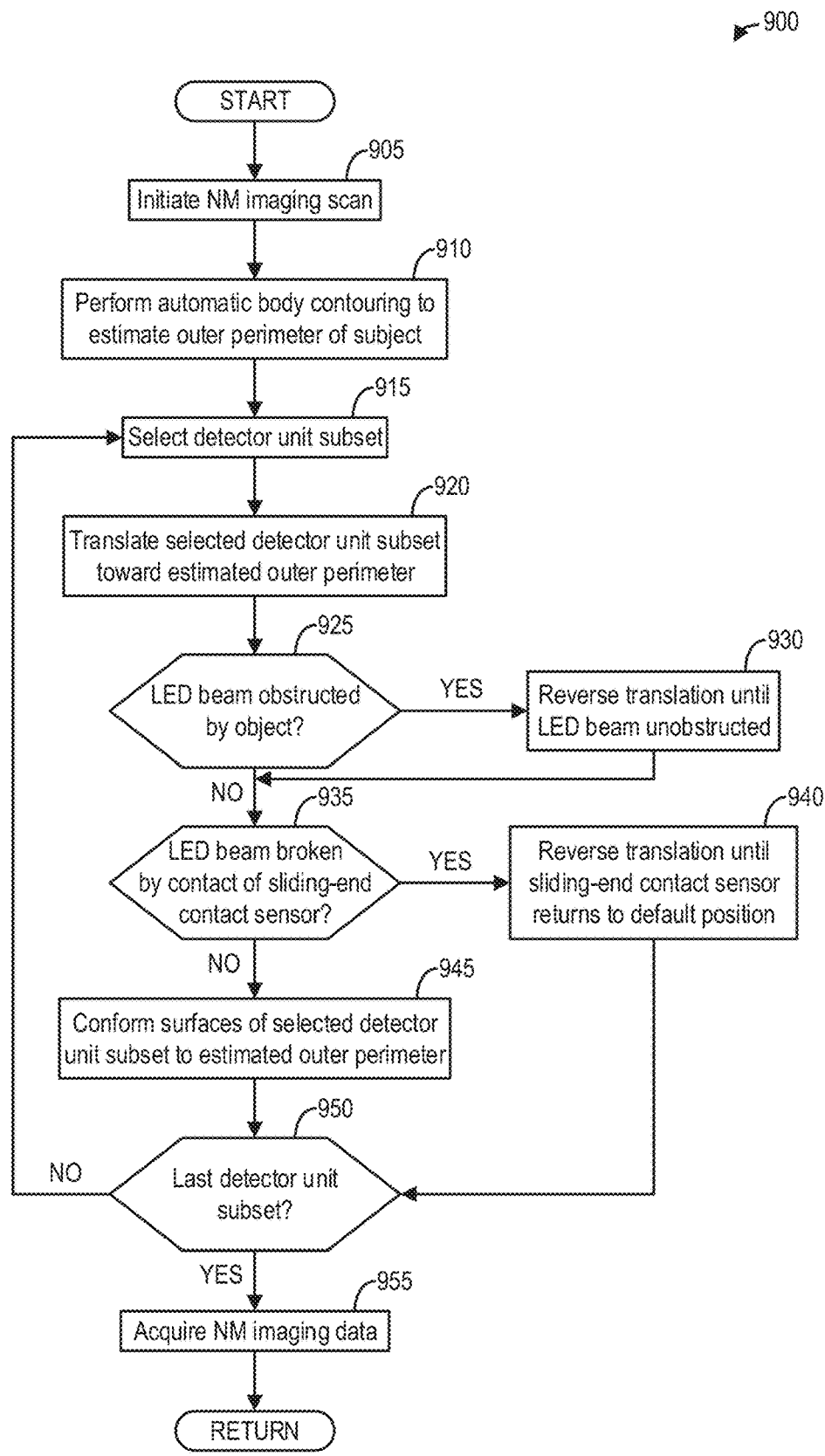
FIG. 9 shows a flow chart of a method for positioning the detector array of the NM imaging system to image a subject, according to an embodiment.

Referring now to FIG. 9, a flow chart is depicted, showing a method 900 for positioning a detector array of an NM imaging system to image a subject. Execution of the method 900 may depend upon various degrees of freedom via which detector units of the detector array may move, such that the detector units are positioned to optimally image a subject. As such, in some examples, method 900 may be used in place of 810 and 815 of method 800, whereby method 800 may continue at 820 following completion of method 900.

Method 900 is described below with regard to the systems and components depicted in FIGS. 1 and 2, though it should be appreciated that method 900 may be implemented with other systems and components without departing from the scope of the present disclosure. In some embodiments, method 900 may be implemented as executable instructions in any appropriate combination of the NM imaging system 100, an edge device (e.g., an external computing device) connected to the NM imaging system 100, a cloud in communication with the NM imaging system 100, and so on. As one example, method 900 may be implemented in non-transitory memory of a computing device, such as the processing unit 150 of the NM imaging system 100 in FIG. 1 (e.g., in communication with the controller unit 130 of the NM imaging system 100).

Method 900 may begin at 905, where an NM imaging scan may be initiated. The NM imaging scan may include receiving incoming radiation from the subject (e.g., 110) at the detector units (e.g., 114). However, each of the detector units may not yet be positioned for optimal imaging by the NM imaging system (e.g., 100). As such, method 900, from 910 to 950, may include determining a final position for the detector units prior to actively acquiring NM imaging data at 955.

Such a determination of the final position for the detector units (e.g., 114) may begin at 910, where method 900 may include performing an automatic body contouring routine to estimate an outer perimeter of the subject (e.g., 110). For example, sensors included in at least one detector unit may be operable to receive optical feedback based on external surfaces of the subject. As such, an approximate location of the subject and a volume thereof may be determined, such that the outer perimeter relative to a location of a given detector unit including the sensors may be estimated.

At 915, method 900 may include selecting one subset of detector units (e.g., 114) of the detector array (e.g., 106). It will be appreciated that, though 915 to 950 are directed to sequential adjustment of positions of various subsets of detector units in the detector array, 915 to 950 may be executed simultaneously for each given subset of detector units in the detector array (e.g., each of the subsets of detector units in the detector array may be positioned simultaneously to one another).

At 920, method 900 may include translating the selected subset of detector units (e.g., 114) toward the estimated outer perimeter. Translation of the selected subset of detector units may include moving along various degrees of freedom (e.g., the axes of rotation and translation as described above with reference to FIG. 3) to closely approximate the estimated outer perimeter. Further, though the selected subset of detector units may be carried by respective detector carriers (e.g., 116) along a track (such as the track 304 as described above with reference to FIG. 3) of the gantry (e.g., 104) parallel to the subject (e.g., 110), the detector units within the selected subset may individually move inwards toward the subject. However, in some examples, since portions of the estimated outer perimeter may lie within an actual perimeter of the subject, a given detector unit within the selected subset may attempt to move to a position which may result in the given detector unit contacting the subject, possibly causing the subject discomfort and subjecting the various components of the given detector unit to undue pressure. As such, proximity of the given detector unit to an object (e.g., the subject or another detector unit) may be detected by interruption of the LED beam (e.g., 218) projected between the pair of optical detectors (e.g., 216a, 216b) included in the given detector unit and remedied accordingly.

For example, at 925, method 900 may include determining whether the LED beam (e.g., 218) of a detector unit (e.g., 114) in the selected subset is obstructed by a first object. Specifically, the detector unit may include two proximity detectors (e.g., 215), each proximity detector respectively including one sliding-end contact sensor (e.g., 214) and one optical sensor (e.g., 216a, 216b). The optical sensors may be disposed opposite one another, such that one of the optical sensors may generate the LED beam for the other optical sensor to receive. Obstruction of the LED beam may therefore indicate that the detector unit is too close to the first object, such as the subject (e.g., 110) or another detector unit.

Thus, if the LED beam (e.g., 218) is obstructed by the first object, method 900 may proceed to 930 to reverse translation of the detector unit (e.g., 114) until the LED beam is unobstructed. Specifically, in examples wherein the first object is the subject (e.g., 110), the detector carrier (e.g., 116) mechanically coupled to the detector unit may retract the detector unit by a predetermined distance selected to retain high imaging resolution while minimizing discomfort to the subject and pressure applied to the detector unit.

If the LED beam (e.g., 218) is not obstructed by the first object, or if the detector unit (e.g., 114) has been retracted by the corresponding detector carrier (e.g., 116), method 900 may proceed to 935 to determine whether the LED beam of a detector unit in the selected subset is broken by contact of one of the sliding-end contact sensors (e.g., 214) with a second object. The sliding-end contact sensors may be disposed at corners adjacent to the surface (e.g., 115) of the detector unit facing the subject, whereby a given sliding-end contact sensor may be actuated (e.g., depressed) when the detector unit translates toward, and then contacts, the second object. Actuation of the sliding-end contact sensor may therefore indicate that the detector unit is too close to the second object, such as the subject (e.g., 110) or another detector unit. In some embodiments, the second object may be different from the first object. In other embodiments, the second object may be the first object.

If the LED beam (e.g., 218) is broken by contact of one of the sliding-end contact sensors (e.g., 214) with the second object, method 900 may proceed to 940 to reverse translation of the detector unit (e.g., 114) until the sliding-end contact sensor returns to a default (e.g., unactuated and non-depressed) position. Specifically, since each sliding-end contact sensor may be mechanically coupled to one of the optical sensors (e.g., 216a, 216b), upon actuation the LED beam between the optical sensors may be broken. Reversing translation of the detector unit may free the sliding-end contact sensor from contact with the second object. Accordingly, the sliding-end contact sensor may return to the default position and a path of the LED beam may be restored (that is, one of the optical sensors may again receive the LED beam projected by the other optical sensor). Further, in examples wherein the second object is the subject (e.g., 110), reversing translation only until the sliding-end contact sensor returns to the default position may maintain a proximity of the detector unit to the subject, thereby retaining high imaging resolution while minimizing discomfort to the subject and pressure applied to the detector unit.

If the LED beam (e.g., 218) is not broken by contact of one of the sliding-end contact sensors (e.g., 214) with the second object, method 900 may proceed to 945 to conform the surfaces (e.g., 115) of the selected subset of detector units (e.g., 114) facing the subject (e.g., 110) to the estimated outer perimeter. Said another way, the NM imaging system (e.g., 100) may be operable to conform the selected subset of detector units conform to the estimated outer perimeter upon determination of no obstructing objects preventing such conformation.

Once the surfaces (e.g., 115) of the selected subset of detector units (e.g., 114) facing the subject (e.g., 110) have been conformed to the estimated outer perimeter, or if translation of one or more of the selected subset of detector units has been reversed to return corresponding sliding-end contact sensor(s) (e.g., 214) to default position(s) thereof, method 900 may proceed to 950 to determine whether the selected subset of detector units is a last subset of detector units in the detector array (e.g., 106) to be positioned. If the selected subset of detector units is not the last subset of detector units, method 900 may return to 915 to select another subset of detector units for positioning.

If the selected subset of detector units (e.g., 114) is the last subset of detector units, the detector array (e.g., 106) may be considered in position for optimal imaging. Thus, during the NM imaging scan, the incoming radiation may pass through, and be narrowed by, the collimators (e.g., 122) associated with the various detector units. The incoming radiation may be passed to respective CZT modules (e.g., 204) such that, at 955, the NM imaging data may be acquired. Method 900 may then end.

In this way, an adjustable detector array is provided for a nuclear medicine (NM) imaging system. In some embodiments, the adjustable detector array may include a plurality of detector units, which may respectively translate via a plurality of detector carriers to conform to a patient to decrease an amount of "dead shielding" space, thereby increasing an imaging sensitivity of the NM imaging system. Specifically, the plurality of detector carriers may rotate around a gantry via a rectangular track such that the plurality of detector units may be adjusted to a location of a patient or a region of interest thereof. A technical effect of mounting the plurality of detector carriers in the rectangular track of the gantry is that an increased number of detector units may be disposed on the gantry without obstructing or obscuring each other as compared to a gantry having a circular track. Further, each of the plurality of detector units may include sliding-end contact sensors paired with additional optical sensors. A technical effect of including the sliding-end contact sensors and the additional optical sensors is that the NM imaging system may detect when a given detector unit is within a threshold distance of the patient to be imaged, and may make corresponding adjustments to mitigate patient discomfort. Additionally, each of the plurality of detector units may include multiple rows of cadmium zinc telluride (CZT) modules interfaced with an exchangeable collimator for acquiring imaging data (e.g., receiving photons). A technical effect of including multiple rows of CZT modules (as opposed to a single row) is that the imaging sensitivity of the NM imaging system may be increased. Further, the exchangeable collimator may provide imaging flexibility, as different collimators may be fit to the plurality of detector units depending on imaging application. As a result of the increased imaging sensitivity and flexibility, fewer detector units may be employed to achieve a given imaging resolution, thereby reducing an overall cost of the NM imaging system.

In one embodiment, a detector array comprises a plurality of adjustable imaging detectors arranged in subsets thereof, each of the plurality of adjustable imaging detectors comprising a detector unit, each detector unit having a plurality of rows of detector modules, wherein the plurality of adjustable imaging detectors are arranged on an annular gantry, where an inner surface of the annular gantry circumscribes a substantially rectangular aperture therethrough, and wherein each subset of the plurality of adjustable imaging detectors is respectively disposed on a side of the inner surface and extends within the substantially rectangular aperture. In a first example of the detector array, each detector unit is parallel or perpendicular to each other detector unit and each side of the inner surface. In a second example of the detector array, optionally including the first example of the detector array, the annular gantry comprises a track circumscribed by the inner surface, and each subset of the plurality of adjustable imaging detectors are positioned partially within the track such that each subset of the plurality of adjustable imaging detectors is operable to move independently along the track with respect to each other subset of the plurality of adjustable imaging detectors. In a third example of the detector array, optionally including one or more of the first and second examples of the detector array, each of the plurality of adjustable imaging detectors comprises a telescoping detector carrier, where each detector unit is respectively positioned at an end of each telescoping detector carrier nearest a first axis extending a length of the substantially rectangular aperture and each telescoping detector carrier is configured to extend toward or retract from the first axis. In a fourth example of the detector array, optionally including one or more of the first through third examples of the detector array, each detector unit is respectively affixed to the end of each telescoping detector carrier, such that each detector unit remains in a fixed position relative to the end of a corresponding telescoping detector carrier. In a fifth example of the detector array, optionally including one or more of the first through fourth examples of the detector array, a first axis is located at a center of the substantially rectangular aperture, the first axis extending a length of the substantially rectangular aperture, and the annular gantry is configured for full rotation about the first axis. In a sixth example of the detector array, optionally including one or more of the first through fifth examples of the detector array, each detector module is a cadmium zinc telluride module. In a seventh example of the detector array, optionally including one or more of the first through sixth examples of the detector array, each detector unit comprises three rows of detector modules, and each of the three rows of detector modules comprises seven detector modules. In an eighth example of the detector array, optionally including one or more of the first through seventh examples of the detector array, the plurality of adjustable imaging detectors comprise at least ten adjustable imaging detectors and at most eighteen adjustable imaging detectors, and the plurality of adjustable imaging detectors comprise an even number of adjustable imaging detectors. In a ninth example of the detector array, optionally including one or more of the first through eighth examples of the detector array, each of the plurality of adjustable imaging detectors has a same configuration as each other adjustable imaging detector. In a tenth example of the detector array, optionally including one or more of the first through ninth examples of the detector array, each detector unit comprises a pair of proximity detectors disposed opposite to one another, a first one of the pair of proximity detectors comprises a first optical sensor configured to project a light-emitting diode (LED) beam, a second one of the pair of proximity detectors comprises a second optical sensor configured to receive the LED beam, and upon interruption of the LED beam by an interfering object, the detector unit is configured to retract and/or pivot away from the interfering object. In an eleventh example of the detector array, optionally including one or more of the first through tenth examples of the detector array, each of the pair of proximity detectors comprises a sliding-end contact sensor, and upon application of a threshold pressure to any sliding-end contact sensor by the interfering object, the LED beam is interrupted. In a twelfth example of the detector array, optionally including one or more of the first through eleventh examples of the detector array, each detector unit comprises an exchangeable collimator, the exchangeable collimator selected for a particular imaging application.

In another embodiment, a medical imaging system comprises an annular gantry having an inner surface circumscribing a substantially rectangular aperture, a detector array positioned on the annular gantry, the detector array comprising subsets of detector units extending within the substantially rectangular aperture from respective sides of the inner surface, each detector unit comprising a plurality of rows of cadmium zinc telluride modules registered with an exchangeable collimator for receiving incoming radiation from a subject positioned within the substantially rectangular aperture, and a processing unit configured with instructions in non-transitory memory that when executed cause the processing unit to coordinate the subsets of detector units to move to a first position to receive the incoming radiation from the subject, and acquire medical imaging data from the subsets of detector units based on the incoming radiation. In a first example of the medical imaging system, the processing unit is further configured to perform an automatic body contouring routine to estimate an outer perimeter of the subject, and coordinating the subsets of detector units comprises translating the subsets of detector units toward the estimated outer perimeter. In a second example of the medical imaging system, optionally including the first example of the medical imaging system, each detector unit comprises a plurality of proximity detectors configured to, upon detecting the subject within a threshold distance of a corresponding detector unit, retract and/or pivot the corresponding detector unit away from the subject. In a third example of the medical imaging system, optionally including one or more of the first and second examples of the medical imaging system, the processing unit is further configured to determine an angular resolution of the imaging data, and responsive to an insufficient angular resolution being determined, retract the subsets of detector units from the subject, shift each subset of detector units relative to the subject by a resolution length, coordinate the subsets of detector units to move to a second position to receive further incoming radiation from the subject, and acquire further imaging data from the subsets of detector units based on the further incoming radiation.

In yet another embodiment, a method for medical imaging comprises positioning a subject within a substantially rectangular aperture of an annular gantry, where each of a plurality of sides of an inner surface of the annular gantry circumscribing the substantially rectangular aperture is respectively configured with a subset of imaging detectors, each of the imaging detectors comprises a detector unit, each detector unit comprises an exchangeable collimator positioned adjacent to three rows of cadmium zinc telluride (CZT) modules, each exchangeable collimator is configured to receive and narrow incoming radiation from an area within the subject for each corresponding CZT module, and each row of CZT modules remains parallel to one of the plurality of sides of the inner surface throughout the medical imaging, estimating an outer perimeter of the subject, translating the subsets of imaging detectors toward the estimated outer perimeter, acquiring nuclear medicine (NM) imaging data based on the incoming radiation, and diagnosing a medical issue afflicting the area within the subject based on the NM imaging data. In a first example of the method, each detector unit comprises a pair of optical sensors projecting a light-emitting diode (LED) beam therebetween, and the method comprises, responsive to any LED beam being obstructed by the subject, translating a corresponding detector unit away from the subject until the LED beam is unobstructed. In a second example of the method, optionally including the first example of the method, each detector unit comprises a pair of sliding-end contact sensors respectively coupled to the pair of optical sensors, and the method comprises, responsive to any LED beam being broken as a result of one of a corresponding pair of sliding-end contact sensors being contacted by the subject, translating a corresponding detector unit away from the subject until the one of the corresponding pair of sliding-end contact sensors returns to a default position.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising." "including." or "having" an element or a plurality of elements having a particular property may include additional such elements not having that property. The terms "including" and "in which" are used as the plain-language equivalents of the respective terms "comprising" and "wherein." Moreover, the terms "first." "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:
1. A detector array, comprising:
a plurality of adjustable imaging detectors arranged in subsets thereof,
  each of the plurality of adjustable imaging detectors comprising:
    a movable detector carrier; and
    a detector unit affixed to a distal end of the movable detector carrier, wherein each detector unit has a plurality of rows of detector modules,
wherein the plurality of adjustable imaging detectors is configured to be coupled to an annular gantry having an inner surface that circumscribes a substantially rectangular aperture therethrough such that:
  each of the subsets is arranged such that movable detector carriers of the plurality of adjustable imaging detectors move parallel to each other,
wherein the subsets are arranged in opposing pairs,
wherein the movable detector carriers of subsets within one pair move substantially parallel to each other, and substantially perpendicular to the movable detector carriers of subsets within another pair, and
wherein each subset of the plurality of adjustable imaging detectors is respectively disposed on a side of the inner surface and extends within the substantially rectangular aperture.

2. The detector array of claim 1, wherein
the annular gantry comprises a track circumscribed by the inner surface, and
each subset of the plurality of adjustable imaging detectors is positioned partially within the track such that each subset of the plurality of adjustable imaging detectors is operable to move independently along the track with respect to each other subset of the plurality of adjustable imaging detectors.

3. The detector array of claim 1, wherein each of the plurality of adjustable imaging detectors further comprises a telescoping detector carrier, where each detector unit is respectively positioned at an end of each telescoping detector carrier nearest a first axis extending a length of the substantially rectangular aperture, and each telescoping detector carrier is configured to extend toward or retract from the first axis.

4. The detector array of claim 3, wherein each detector unit is respectively affixed to the end of each telescoping detector carrier, such that each detector unit remains in a fixed position relative to the end of a corresponding telescoping detector carrier.

5. The detector array of claim 1, wherein
a first axis is located at a center of the substantially rectangular aperture, the first axis extending a length of the substantially rectangular aperture, and
the annular gantry is configured for a full rotation about the first axis.

6. The detector array of claim 1, wherein each of the plurality of rows of detector modules is a cadmium zinc telluride module.

7. The detector array of claim 1, wherein
each detector unit comprises three rows of detector modules, and
each of the three rows of detector modules comprises seven detector modules.

8. The detector array of claim 1, wherein
the plurality of adjustable imaging detectors comprise at least ten adjustable imaging detectors and at most eighteen adjustable imaging detectors, and
the plurality of adjustable imaging detectors comprise an even number of adjustable imaging detectors.

9. The detector array of claim 1, wherein each of the plurality of adjustable imaging detectors has a same configuration as each other adjustable imaging detector.

10. The detector array of claim 1, wherein
each detector unit comprises a pair of proximity detectors disposed opposite to one another,
a first one of the pair of proximity detectors comprises a first optical emitter configured to project a light-emitting diode (LED) beam,
a second one of the pair of proximity detectors comprises a second optical sensor configured to receive the LED beam, and
upon an interruption of the LED beam by an interfering object, each detector unit is configured to retract and/or pivot away from the interfering object.

11. The detector array of claim 10, wherein
each of the pair of proximity detectors comprises a sliding-end contact sensor, and
upon an application of a threshold pressure to either sliding-end contact sensor by the interfering object, the LED beam is interrupted.

12. The detector array of claim 1, wherein each detector unit comprises an exchangeable collimator, the exchangeable collimator selected for a particular imaging application.

13. A medical imaging system, comprising:
an annular gantry having an inner surface circumscribing a substantially rectangular aperture;
a detector array positioned on the annular gantry, the detector array comprising subsets of detector units extending within the substantially rectangular aperture from respective sides of the inner surface, each detector unit comprising a plurality of rows of cadmium zinc telluride modules, wherein each of the plurality of rows of cadmium zinc telluride modules comprises a two-dimensional array of pixels;
an exchangeable collimator comprising bores for receiving incoming radiation from a subject positioned within the substantially rectangular aperture, wherein the bores of the exchangeable collimator are registered to the two-dimensional array of pixels of corresponding cadmium zinc telluride modules; and
a processing unit configured with instructions in a non-transitory memory that when executed cause the processing unit to:
coordinate the subsets of detector units to move to a first position to receive the incoming radiation from the subject, and
acquire medical imaging data from the subsets of detector units based on the incoming radiation.

14. The medical imaging system of claim 13, wherein the processing unit is further configured to:
perform an automatic body contouring routine to estimate an outer perimeter of the subject; and
coordinate the subsets of detector units to move to the first position by translating the subsets of detector units toward the estimated outer perimeter.

15. The medical imaging system of claim 13, wherein each detector unit comprises a plurality of proximity detectors configured to, upon detecting the subject within a threshold distance of a corresponding detector unit, retract and/or pivot the corresponding detector unit away from the subject.

16. The medical imaging system of claim 13, wherein the processing unit is further configured to:
determine an angular resolution of the medical imaging data; and
responsive to an insufficient angular resolution of the medical imaging data being determined:
retract the subsets of detector units from the subject,
shift each subset of the subsets of detector units relative to the subject by a resolution length,
coordinate the subsets of detector units to move to a second position to receive further incoming radiation from the subject, and
acquire further medical imaging data from the subsets of detector units based on the further incoming radiation.

17. A method for medical imaging, the method comprising:
positioning a subject within a substantially rectangular aperture of an annular gantry, where each of a plurality of sides of an inner surface of the annular gantry circumscribing the substantially rectangular aperture is respectively configured with a subset of imaging detectors, each of the subsets of imaging detectors comprises a detector unit, each detector unit comprises an exchangeable collimator positioned adjacent to three rows of cadmium zinc telluride (CZT) modules, each exchangeable collimator is configured to receive and narrow incoming radiation from an area within the subject for each corresponding CZT module, and each row of the three rows of CZT modules remains parallel to one of the plurality of sides of the inner surface of the annular gantry throughout the medical imaging;
estimating an outer perimeter of the subject;
translating the subset of imaging detectors for each of the plurality of sides of the inner surface of the annular gantry toward the estimated outer perimeter of the subject;
acquiring nuclear medicine (NM) imaging data based on the incoming radiation from the area within the subject; and
diagnosing a medical issue afflicting the area within the subject based on the NM imaging data.

18. The method of claim 17, wherein
each detector unit comprises a pair of optical sensors projecting a light-emitting diode (LED) beam therebetween, and
the method further comprises:
responsive to the LED beam being obstructed by the subject, translating a corresponding detector unit away from the subject until the LED beam is unobstructed.

19. The method of claim 18, wherein
each detector unit comprises a pair of sliding-end contact sensors respectively coupled to the pair of optical sensors, and the method further comprises:
responsive to the LED beam being broken as a result of one of a corresponding pair of sliding-end contact sensors being contacted by the subject, translating a corresponding detector unit away from the subject until the one of the corresponding pair of sliding-end contact sensors returns to a default position.

* * * * *